United States Patent
Dubowchik et al.

(10) Patent No.: US 6,818,643 B1
(45) Date of Patent: Nov. 16, 2004

(54) NEUROTROPHIC BICYCLIC DIAMIDES

(75) Inventors: Gene Michael Dubowchik, Middlefield, CT (US); David Paul Provencal, Cromwell, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 632 days.

(21) Appl. No.: 09/717,563

(22) Filed: Nov. 21, 2000

Related U.S. Application Data

(60) Provisional application No. 60/169,600, filed on Dec. 8, 1999.

(51) Int. Cl.[7] ................. C07D 471/08; C07D 487/08; A61K 31/439; A61K 31/4995

(52) U.S. Cl. ............... 514/249; 514/300; 544/349; 546/121

(58) Field of Search ................. 514/249, 300; 544/349; 546/121

(56) References Cited

U.S. PATENT DOCUMENTS

| | | | |
|---|---|---|---|
| 5,192,773 A | 3/1993 | Armistead et al. | |
| 5,330,993 A | 7/1994 | Armistead et al. | |
| 5,516,797 A | 5/1996 | Armistead et al. | |
| 5,622,970 A | 4/1997 | Armistead et al. | |
| 5,696,135 A | 12/1997 | Steiner et al. | |
| 5,721,256 A | 2/1998 | Hamilton et al. | |
| 5,780,484 A | 7/1998 | Zelle et al. | |
| 5,786,378 A | 7/1998 | Hamilton et al. | |
| 5,795,908 A | 8/1998 | Hamilton et al. | |
| 5,798,355 A | 8/1998 | Steiner et al. | |
| 5,801,187 A | 9/1998 | Li et al. | |
| 5,801,197 A | 9/1998 | Steiner et al. | |
| 6,630,472 B1 * | 10/2003 | Katoh et al. ............... 514/249 |

FOREIGN PATENT DOCUMENTS

| | | |
|---|---|---|
| EP | 405994 A2 | 1/1991 |
| EP | 564924 B1 | 10/1993 |
| WO | WO 92/19593 | 11/1992 |
| WO | WO 95/21313 | 12/1992 |
| WO | WO 94/07858 | 4/1994 |
| WO | WO 96/40140 | 12/1996 |
| WO | WO 96/40633 | 12/1996 |
| WO | WO 96/41609 | 12/1996 |
| WO | WO 97/16190 | 5/1997 |
| WO | WO 97/36869 | 10/1997 |
| WO | WO 98/13343 | 4/1998 |
| WO | WO 98/13355 | 4/1998 |
| WO | WO 98/20891 | 5/1998 |
| WO | WO 98/20892 | 5/1998 |
| WO | WO 98/20893 | 5/1998 |
| WO | WO 98/29116 | 7/1998 |
| WO | WO 98/29117 | 7/1998 |
| WO | WO 99/10340 | 3/1999 |
| WO | WO 99/21552 | 5/1999 |
| WO | WO 00/04020 * | 1/2000 |

OTHER PUBLICATIONS

US 5,654,332, 8/1997, Armistead (withdrawn)

A. Ruhlmann, et al, "Effects of the Immunosuppressive Drugs CsA and FK506 on Intracellular Signalling and Gene Regulation," Immunobiol., 198, pp. 192–206, 1997.

S. L. Schreiber, et al, "Molecular Recognition of Immunophilins and Immunophilin–Ligand Complexes," Tetrahedron, 48(13), pp. 2545–2558, 1992.

T. Wang, et al, "Specific Interaction of Type I Receptors of the TGF–α Family with the Immunophilin FKBP–12," Science, 265, pp. 674–676, 1994.

A. M. Cameron, et al, "FKBP12 Binds the Inositol 1,4, 5–Trisphosphate Receptor at Leucine–Proline(1400–1401) and Anchors Calcineurin to This FK506–Like Domain," J. Biological Chemistry, 272(44), pp. 27582–27588, 1997.

T. Wang, et al, "The Immunophilin FKBP12 Functions as a Common Inhibitor of the TGFα Family Type I Receptors," Cell, 86, pp. 435–444, 1996.

D. S. Yamashita, et al, "Design, Synthesis and Evaluation of Dual Domain FKBP Ligands," Bioorganic & Medicinal Chemistry Letters, 4(2), pp. 325–328, 1994.

D. M. Armistead, et al, "Design, Synthesis and Structure of Non–Macrocyclic Inhibitors of FKBP12, the Major Binding Protein for the Immunosuppressant FK506," Acta Cryst., D51, pp. 522–528, 1995.

W. E. Lyons, et al, "Immunosuppressant FK506 Promotes Neurite Outgrowth in Cultures of PC12 Cells and Sensory Ganglia," Proc. Natl. Acad. Sci. USA, 91, pp. 3191–3195, 1994.

B. G. Gold, et al, "The Immunosuppressant FK506 Increases the Rate of Axonal Regeneration in Rat Sciatic Nerve," J Neuroscience, 15(11), pp. 7509–7516, 1995.

G. S. Hamilton, et al, "Neuroimmunophilin Ligands as Novel Therapeutics for the Treatment of Degenerative Disorders of the Nervous System," Current Pharmaceutical Design, 3, pp. 405–428, 1997.

B. S. Gold, et al, "A Nonimmunosuppressant FKBP–12 Ligand Increases Nerve Regeneration," Experimental Neurology, 147, pp. 269–278, 1997.

S. H. Snyder, et al, "Immunophilins and the Nervous System," Nature Medicine, 1(1), pp. 32–37, 1995.

B. G. Gold, et al, "The Immunosuppressant FK506 Increases GAP–43 mRNA Levels in Axotomized Sensory Neurons," Neuroscience Letters, 241, pp. 25–28, 1998.

(List continued on next page.)

*Primary Examiner*—Bruck Kifle
(74) *Attorney, Agent, or Firm*—Samuel J. DuBoff

(57) ABSTRACT

The present invention relates to the design, synthesis, and the peptidyl-prolyl isomerase (PPIase or rotamase) inhibitory activity of novel bicyclic diamide compounds that are neuroprotective and/or neurotrophic agents (i.e. compounds capable of stimulating growth or proliferation of nervous tissue) and that bind to immunophilins such as FKBP12 and inhibit their rotamase activity. This invention also relates to pharmaceutical compositions comprising these compounds.

7 Claims, No Drawings

OTHER PUBLICATIONS

B. G. Gold, et al, "Immunophilin FK506–Binding Protein 52 (Not FK506–Binding Protein 12) Mediates the Neurotrophic Action of FK506," Journal of Pharmacology and Experimental Therapeutics, 289(3), pp. 1202–1210, 1999.

C. T. Craescu, et al, "Three–Dimensional Structure of the Immunophilin–Like Domain of FKBP59 in Solution, "Biochemistry, 35, pp. 11045–11052, 1996.

J. R. Hauske, et al, Investigation of the Effects of Synthetic, Non–Cytotoxic Immunophilin Inhibitors on MDR, Bioorganic & Medicinal Chemistry Letters, 4(17), pp. 2097–2102, 1994.

M. M. Endrich, et al, "The V3 Loop the Human Immunodeficiency Virus Type–1 Envelope Protein is a High–Affinity Ligand for Immunophilins Present in Human Blood," Eur. J. Biochem., 252, pp. 441–446, 1998.

A. Karpas, et al, "Inhibition of Human Immunodeficiency Virus and Growth of Infected T Cells by the Immunosuppressive Drugs Cyclosporin A and FK 506." Proc. Natl. Acad. Sci. USA, 89, pp. 8351–8355, 1992.

* cited by examiner

NEUROTROPHIC BICYCLIC DIAMIDES

CROSS-REFERENCE TO RELATED APPLICATION

This application claims the benefit of U.S. Provisional Application No. 60/169,600, filed Dec. 8, 1999.

BACKGROUND OF THE INVENTION

Immunophilins are cytosolic proteins that possess peptidyl-prolyl-cis-trans isomerase (PPIase or rotamase) activity. This family of proteins behave as chaperone molecules causing cis-trans isomerization of peptide-prolyl bonds that could be a rate limiting step in the correct folding of certain proteins. They are also involved in many cellular signal transduction pathways as partners in multiprotein complexes for which binding in the rotamase active site, but not rotamase activity per se, appears to be important (R ühlmann, et al., *Immunobiol.*, 198, pp. 192–206 (1998)). Immunosuppressive drugs such as FK506, rapamycin and cyclosporin A bind to specific groups of immunophilins. FK506 and rapamycin bind to the so-called FK506-binding proteins (FKBPs), whereas the cyclophilins binds to cyclosporin A. It has been shown that binding to the 12 kD immunophilin FKBP12 is necessary for FK506 to elicit its immunosuppressive activity. Subsequently, it was also found that FK506 has two binding domains: one that binds to FKBP12 and the other (the effector domain) for the complex of FK506 and FKBP12 that binds to the serine/threonine phosphatase, calcineurin. This complexation inhibits calcineurin and prevents the proliferation of T-lymphocytes (i.e. immunosuppression). Rapamycin has an effector domain of a different structure, and its complex with FKBP12 binds to a different target protein that, also results in immunosuppression. For a review, see S. L. Schreiber, et al., *Tetrahedron*, 48, pp. 2545–2558 (1992). Some of the other proteins with which FKBP12 is known to interact include the TGFβ receptor I (Wang, et al., *Science*, 265, pp. 674–676 (1994)), the IP$_3$ receptor and the ryanodine receptor (Cameron, et al., *J. Biol. Chem.*, 272, pp. 27582–27588 (1997)). In the case of the TGFβ system, it has been suggested that FKBP12 binding inhibits unregulated signalling with consequences for differentiation, apoptosis and proliferation (Wang, et al., *Cell*, 86, pp. 435–444 (1996)).

While FK506 exhibits immunosuppressive effects, analogs lacking the calcineurin binding effector domain are devoid of immunosuppressive activity. Many small molecules that contain the essential elements of the FKBP12 binding domain of FK506 but lack the calcineurin binding domain were found to retain high affinity binding to FKBP12, and behave as rotamase inhibitors (D. S. Yamshita, et al., *Bioorg. Med. Chem. Lett.*, 4, pp. 325–328 (1994); D. M. Armistead, et al., *Acta Cryst. D*, 51, pp. 522–528 (1995)).

FK506 has been shown to possess neurotrophic properties in vitro and in vivo (W. E. Lyons, et al., *Proc. Natl. Acad. Sci USA*, 91, pp. 3191–3195 (1994); B. G. Gold, et al., *J. Neurosci.*, 15, pp. 7509–7516 (1995)). However, its immunosuppressive properties as well as other serious side effects are drawbacks to its use as a neuroregenerative agent. Recently, in vitro studies in PC12 cells, SY5Y cells, and chick sensory dorsal root ganglion explant cultures have shown that small molecule, nonimmunosuppressive FKBP12 rotamase inhibitors also promote neurite outgrowth, and a number of these compounds have shown utility in reversal of CNS lesioning and nerve crush in animal models (G. S. Hamilton, et al., *Curr. Pharm. Design*, 3, pp. 405–428 (1997); B. G. Gold, et al., *Exp. Neurol.*, 147, pp. 269–278 (1997)). Thus, while the calceineurin binding domain of FK506 is necessary for immunosuppressive activity, it is not required for neurotrophic activity.

A 10–50 fold elevated expression of immunophilins in the central nervous system in comparison with the immune system is well documented (S. H. Snyder, et al., *Nature Med.*, 1, pp. 32–37 (1995)). Recently, augmented expression of FKBP12 m-RNA following facial nerve crush and sciatic nerve lesions was established in facial and lumbar motor neurons. The observed augmentation paralleled the enhanced expression of growth associated protein GAP43 mRNA (B. G. Gold, et al., *Neurosci. Lett.*, 241, pp. 25–28 (1998)). These observations make FKBP12 an attractive target for developing nonimmunosuppressive rotamase inhibitors which promote neurite outgrowth. Such compounds are potential therapeutics to reverse neuronal damage caused by neurodegenerative disease or physical trauma.

Recently, Gold and co-workers (*J. Pharm. Exp. Ther.*, 289, pp. 1202–1210 (1999)) have proposed that neurotrophic FKBP12 binding compounds actually act through binding to the related FK506-binding protein, FKBP52. FKBP52 is known to act as a partner with the chaperone protein hsp90 and p23 in a complex that modulates the activity of steroid receptors. According to this model, compounds such as FK506 that bind to the FKBP52 active site facilitate steroid receptor signaling resulting in neurite growth. Since the FKBP52 rotamase active site is known to be very similar to that of FKBP12 (C. T. Craescu, et al., *Biochemistry*, 35, pp. 11045–11052 (1996)), it is likely that a large proportion of FKBP12-binding compounds will possess neurotrophic activity if this model is valid.

There have been disclosures of related compounds for overcoming multidrug resistance (MDR) or as immunosuppressants such as:

WO 94/07858 published Apr. 14, 1994
WO 92/19593 published Nov. 12, 1992
U.S. Pat. No. 5,622,970 granted Apr. 22, 1997
U.S. Pat. No. 5,330,993 granted Jul. 19, 1994
U.S. Pat. No. 5,192,773 granted Mar. 9, 1993
U.S. Pat. No. 5,516,797 granted May 14, 1996
WO 92/21313 published Dec. 10, 1992
European Application 564924 published Oct. 13, 1993
European Application 405994 published Jan. 2, 1991

Other prior art disclosing related compounds having neurotrophic activity are:

WO 96/40140 published Dec. 19, 1996
WO 96/40633 published Dec. 19, 1996
WO 97/16190 published May 9, 1997
WO 96/41609 published Dec. 27, 1996
U.S. Pat. No. 5,696,135 granted Dec. 9, 1997
WO 97/36869 published Oct. 9, 1997
U.S. Pat. No. 5,721,256 granted Feb. 24, 1998
U.S. Pat. No. 5,654,332 granted Aug. 5, 1997
WO 98/13343 published Apr. 2, 1998
WO 98/13355 published Apr. 2, 1998
WO 98/20891 published May 22, 1998
WO 98/20892 published May 22, 1998
WO 98/20893 published May 22, 1998
WO 98/29116 published Jul. 9, 1998
WO 98/29117 published Jul. 9, 1998
WO 99/10340 published Mar. 4, 1999
WO 99/21552 published May 6, 1999

U.S. Pat. No. 5,780,484 granted Jul. 14, 1998
U.S. Pat. No. 5,786,378 granted Jul. 28, 1998
U.S. Pat. No. 5,795,908 granted Aug. 18, 1998
U.S. Pat. No. 5,798,355 granted Aug. 25, 1998
U.S. Pat. No. 5,801,187 granted Sep. 1, 1998
U.S. Pat. No. 5,801,197 granted Sep. 1, 1998

Since there are relatively few FKBP12-binding compounds that are known to stimulate neurite growth, there remains a great need for additional neurotrophic, FKBP12-binding compounds.

SUMMARY OF THE INVENTION

Surprisingly, applicant has solved the aforementioned problem. The present invention relates to novel bicyclic diamide compounds and pharmaceutical compositions thereof that possess neurotrophic and/or neuroprotective properties.

DETAILED DESCRIPTION OF THE INVENTION

According to one embodiment, the present invention provides:

A compound with affinity for an FK506 binding protein having the formula (I):

(I)

and pharmaceutically acceptable salts thereof, wherein:

X is O or $F_2$;
n is 1 or 2;
m is 0, 1, or 2;
p is 0 or 1;
wherein the stereochemistry at carbon position 1 is R or S;

D is $(C_1-C_6)$-straight or branched alkyl, $(C_2-C_6)$-straight or branched alkenyl, $(C_5-C_7)$-cycloalkyl or $(C_5-C_7)$-cycloalkenyl substituted with $(C_1-C_4)$-straight or branched alkyl or $(C_2-C_4)$-straight or branched alkenyl, O—$(C_1-C_4)$-straight or branched alkyl, O—$(C_2-C_4)$-straight or branched alkenyl, 2-indolyl, 3-indolyl, [$(C_1-C_4)$-alkyl or $(C_2-C_4)$-alkenyl]-Ar or Ar;

Ar is a carbocyclic aromatic group selected from the group consisiting of phenyl, 1-naphthyl, 2-naphthyl, indenyl, azulenyl, fluorenyl, and anthracenyl; or a heterocyclic aromatic group selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl;

Ar may contain one to three substituents which are independently selected from the group consisting of hydrogen, halogen, hydroxyl, hydroxymethyl, nitro, trifluoromethyl, trifluoromethoxy, $(C_1-C_6)$-straight or branched alkyl, $(C_2-C_6)$-straight or branched alkenyl, O—[$(C_1-C_4)$-straight or branched alkyl], O-benzyl, O-phenyl, 1,2-methylenedioxy, amino, carboxyl, N-[$(C_1-C_5)$-straight or branched alkyl or $(C_2-C_5)$-straight or branched alkenyl]carboxamides, N,N-di-[$(C_1-C_5)$-straight or branched alkyl or $(C_2-C_5)$-straight or branched alkenyl] carboxamides, N-morpholinecarboxamide, N-benzylcarboxamide, N-thiomorpholinocarboxamide, N-picolinoylcarboxamide, O—W, $CH_2$—$(CH_2)_q$—W, O—$(CH_2)_q$—W, $(CH_2)_q$—O—W, and CH=CH—W;

W is 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, or pyrimidyl; q is 0–2;

Q and A are independently hydrogen, Ar, $(C_1-C_{10})$-straight or branched alkyl, $(C_2-C_{10})$-straight or branched alkenyl or alkynyl, $(C_5-C_7)$-cycloalkyl substituted $(C_1-C_6)$-straight or branched alkyl, $(C_2-C_6)$-straight or branched alkenyl or alkynyl, $(C_5-C_7)$-cycloalkenyl substituted $(C_1-C_6)$-straight or branched alkyl, $(C_2-C_6)$-straight or branched alkenyl or alkynyl, or Ar-substituted $(C_1-C_6)$-straight or branched alkyl, $(C_2-C_6)$-straight or branched alkenyl or alkynyl wherein, in each case, any one of the $CH_2$ groups of said alkyl, alkenyl or alkynyl chains may be optionally replaced by a heteroatom selected from the group consisting of O, S, SO, $SO_2$, N, and NR, wherein R is selected from the group consisting of hydrogen, $(C_1-C_4)$-straight or branched alkyl, $(C_2-C_4)$-straight or branched alkenyl or alkynyl, and $(C_1-C_4)$-bridging alkyl wherein a bridge is formed between the nitrogen and a carbon atom of said heteroatom-containing chain to form a ring, and wherein said ring is optionally fused to an Ar group; or G is hydrogen, $(C_1-C_6)$-straight or branched alkyl or $(C_2-C_6)$-straight or branched alkenyl or alkynyl; and T is Ar or substituted 5–7 membered cycloalkyl with substituents at positions 3 and 4 which are independently selected from the group consisting of oxo, hydrogen, hydroxyl, O—$(C_1-C_4)$-alkyl, or O—$(C_2-C_4)$-alkenyl.

A preferred embodiment are compounds of formula I wherein the stereochemistry at carbon 1 is S;
m is 0 or 1;
n is 1;
p is 1;
X is O or $F_2$;
Z is O or $CH_2$;
D is 3,4,5-trimethoxyphenyl or t-pentyl;
Q and A are independently hydrogen; 2, 3, or 4-pyridyl; or phenyl-substituted $(C_1-C_6)$-straight or branched chain alkyl, wherein phenyl is optionally substituted with one to three substituents independently selected from ($C_1$–$C_6$) alkyl, O—($C_1$–$C_6$) alkyl, carboxyl and trifluoromethyl, wherein said alkyl is straight or branched.

Another preferred embodiment are compounds of formula I wherein
X is O;
m is 1;
n is 1;
p is 1;
A is
3-phenylpropyl;
2-phenylethyl;
2-(3,4-dimethoxyphenylethyl;
3-(3,4,5-trimethoxyphenyl)propyl;
3-(3,4-dimethoxyphenyl)propyl;
Q is
3-phenylpropyl;
2-phenylethyl;
3-(3,4,5-trimethoxyphenyl)propyl;
2-(3,4-dimethoxyphenyl)ethyl;
3-(3,4-dimethoxyphenyl)propyl.

Another preferred embodiment are compounds of formula I wherein
X is O;
m is 1;
n is 1;
p is 0;
A is hydrogen;
Q is
2-(3,4,5-triethoxyphenyl)ethyl;
2-(3,4-dimethoxyphenyl)ethyl;
3-(3,4-dimethoxyphenyl)propyl;
2-phenylethyl;
3-phenylpropyl;
4-phenylbutyl;
2-(3-pyridyloxy)ethyl;

Another preferred embodiment are compounds of formula I wherein
X is O;
m is 1;
n is 0;
p is 1;
A is
3-phenylpropyl;
2-phenylethyl;
2-(3,4-dimethoxyphenyl)ethyl;
3-(3,4,5-trimethoxyphenyl)propyl;
3-(3,4-dimethoxyphenyl)propyl;
Q is
3-phenylpropyl;
2-phenylethyl;
3-(3,4,5-trimethoxyphenyl)propyl;
2-(3,4-dimethoxyphenyl)ethyl;
3-(3,4-dimethoxyphenyl)propyl.

Another preferred embodiment are compounds of formula I wherein
X is O;
m is 1;
n is 0;
p is 0;
A is hydrogen;
Q is
2-(3,4,5-trimethoxyphenyl)ethyl;
2-(3,4-dimethoxyphenyl)ethyl;
3-(3,4-dimethoxyphenyl)propyl;
2-phenylethyl;
3-phenylpropyl;
4-phenylbutyl;
2-(3-pyridyloxy)ethyl;

Another aspect of the present invention provides for a pharmaceutical composition which comprises as an active ingredient an amount of a compound of formula I, or a pharmaceutically acceptable salt thereof, effective for stimulating neurite growth in nerve cells, and one or more pharmaceutically acceptable carriers, excipients or diluents thereof.

Another aspect of the present invention provides for a method for stimulating neurite growth in nerve cells comprising the step of contacting said nerve cells with a composition comprising a neurotrophic amount of a compound of formula I with affinity for an FK-506 binding protein.

Another aspect of the present invention provides for a method for stimulating neurite growth in nerve cells comprising the step of contacting said nerve cells with a composition comprising a neurotrophic amount of a compound of formula I with affinity for FKBP12.

GENERAL SUMMARY OF COMPOUND PREPARATION

The bicyclic diamides of this invention are best prepared according to the general scheme shown below. The amides are alkylated using sodium hydride and an appropriate halide to give the N-alkylated products. The resulting compounds were treated with either hydrogen chloride, to remove t-butyloxycarbonyl (Boc) protecting groups, or ammonium formate and palladium on carbon, to remove benzyl protecting groups, and then acylated to give the target compounds.

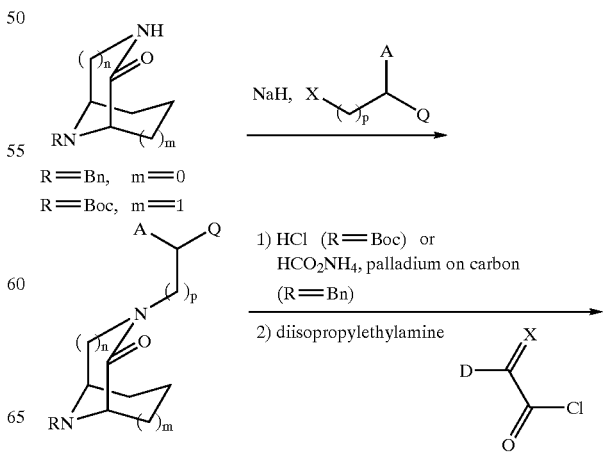

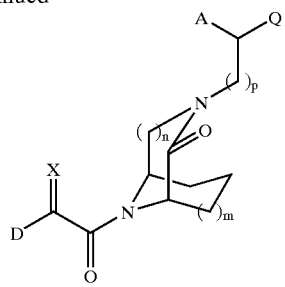

Additionally, addition of an appropriate Grignard reagent to the ester-amide can give the ketoamide targets.

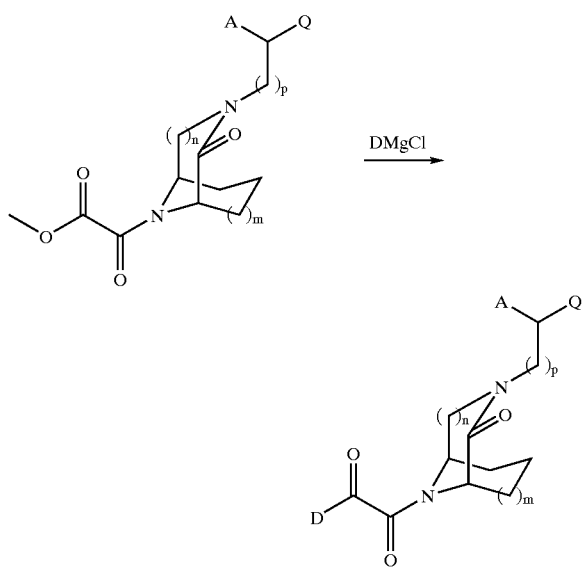

The bicyclic core structures can be prepared by first benzylation of the amide nitrogen and then conversion to the thioamide using Lawesson's reagent. Treatment of the thioamide with iodomethane produces the thiomethylimmonium iodide. Condensation with nitromethane and excess triethylamine generates the nitroenamine. Finally, hydrogenation with palladium on carbon affords the desired bicyclic compounds.

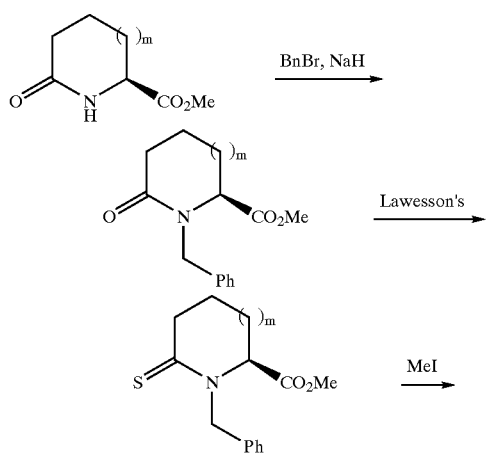

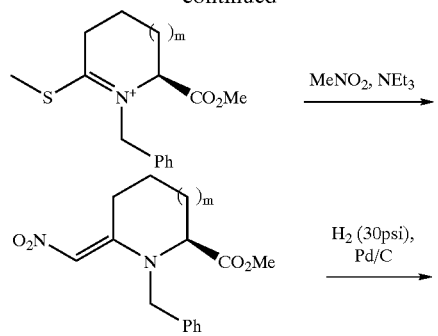

The bicyclic core structure can also be synthesized by the general scheme below. In a three step sequence, the Boc protected amide is partially reduced to the hemiaminal using lithium triethylborohydride and then converted to the α-methoxy lactam using catalytic p-toluenesulfonic acid in methanol. Lewis acid catalyzed substitution using trimethylsilylcyanide gives the nitrile. Platinium oxide catalyzed reduction of the nitrile followed by treatment with triethylamine gives the desired bicyclic core systems.

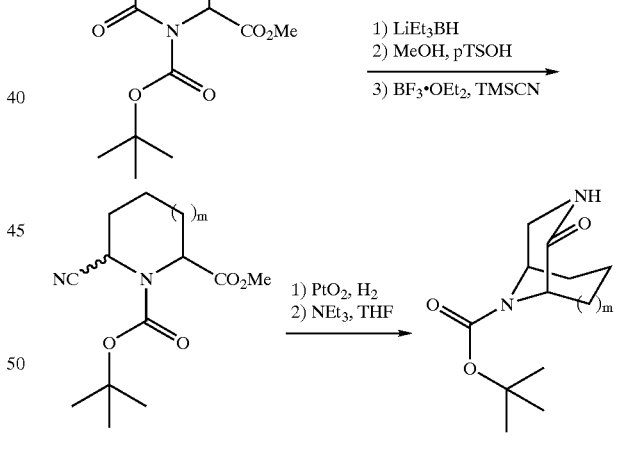

The requisite 6-oxopipecolate is synthesized from methyl pipecolate by acylation of the amine with di-t-butyl carbonate followed by ruthenium catalyzed oxidation to yield the desired compound.

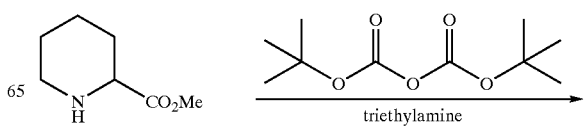

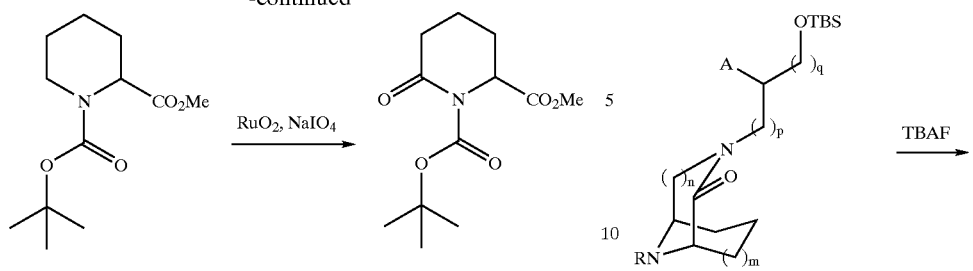

The following scheme illustrates how the halides for the amide alkylation are best prepared. The unbranched compounds are generated directly from the alcohol using carbon tetrabromide and triphenylphosphine. When p=0, the compounds are best prepared by oxidation to the aldehyde and addition of grignard reagents. The resulting alcohol is then converted to the secondary iodide.

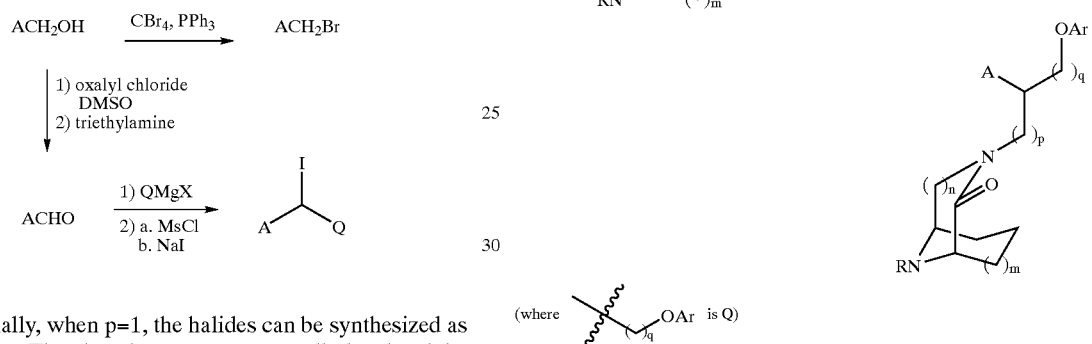

Additionally, when p=1, the halides can be synthesized as shown below. The phosphonate was mono-alkylated and the product was used in a Homer-Emmons reaction to afford the trisubstituted olefins. The olefin was hydrogenated using palladium catalyst, the ester reduced to the alcohol with lithium aluminum hydride, and then converted to the halide to provide the necessary side-chain.

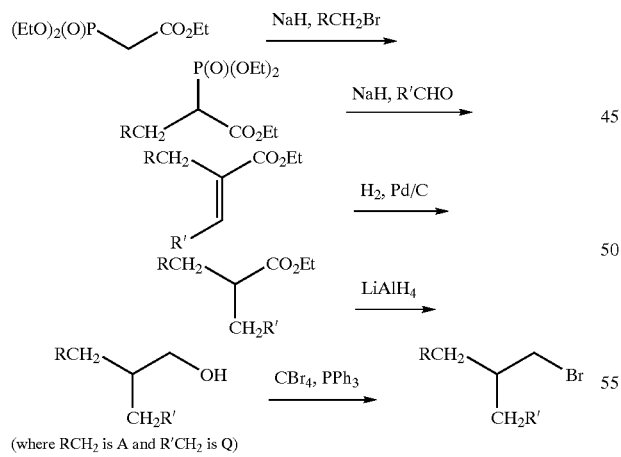

The side-chains containing oxygen substitution can be prepared the manner shown the in the following scheme. The silyl protecting group is removed by treatment with tetrabutylammonium fluoride to give the free alcohol. Standard Mitsunobu reaction generates the products. The Mitsunobu reaction can be carried out on the N-protected intermediates or with the ketoamide already in place.

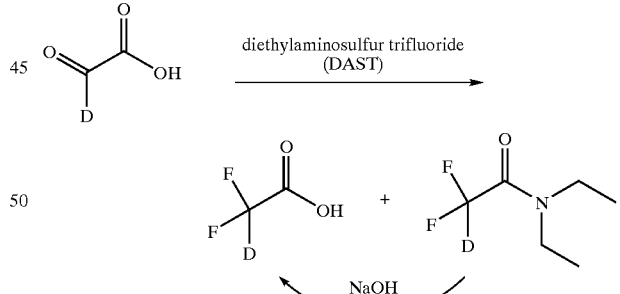

The 2,2-difluoroacetic acids are synthesized by fluorination of the parent ketone compound with diethylaminosulfurtrifluoride. The N,N-diethylamides are sometimes also obtained in small amounts, but are easily converted to the desired acid by alkaline hydrolysis.

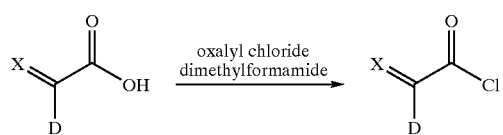

The acids are converted to the corresponding acid chlorides using oxalyl chloride and catalytic dimethylformamide in methylene chloride.

PREPARATION OF INTERMEDIATES 3,4,5-Trimethoxyphenyl-2-oxoacetyl chloride

A stirred suspension of 3,4,5-trimethoxyphenyl-2-oxoacetic acid (1.60 g, 6.66 mmoles) in dry methylene chloride (26 mL) at room temperature was treated with 2M oxalyl chloride in methylene chloride (14 mL, 4 equiv.) and dry dimethylformamide (1 drop). After 3 h the solvents were evaporated. The residue was flushed with dry methylene chloride (3×50 mL) and dried in vacuo for 2 h during which time a solid formed. The crude acid chloride was carried on without further purification.

α,α-Difluoro-3,4,5-trimethoxyphenylacetyl chloride

This was prepared as described above for 3,4,5-trimethoxyphenyl-2-oxoacetyl chloride from the corresponding carboxylic acid and was used without chromatographic purification.

1,5-Diphenyl-3-iodopentane

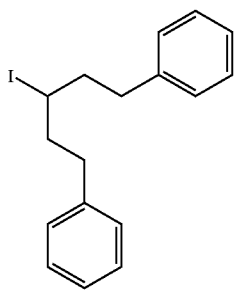

To a solution of 1,5-diphenyl-3-propanol (0.978 g, 4.07 mmol) and triethylamine (1.15 mL, 8.25 mmol) in methylene chloride (20 mL) was added dropwise methanesulfonyl chloride (0.500 mL, 6.46 mmol) at −5° C., and the resulting solution was stirred at −5° C. for 2 h. The organic layer was washed with water, 1N HCl, saturated aqueous sodium bicarbonate, brine, and dried over magnesium sulfate. The solvent was removed under reduced pressure and the residue was dissolved acetone (25 mL). Sodium iodide (1.85 g, 12.3 mmol) was added and the resulting mixture was heated to reflux under nitrogen for 18 h. The solvent was removed under reduced pressure and the residue was partitioned between water and methylene chloride. The organic layer was washed with water, dried over magnesium sulfate, and concentrated in vacuo. The crude product was purified by silica gel chromatography, eluting with ethyl acetate/hexanes (1% to 2%), to provide 1,5-diphenyl-3-iodopentane (1.03 g, 72%). $^1$H NMR (300 MHz, CDCl$_3$): δ 2.17 (m, 2 H), 2.25 (m, 2 H), 2.76, (m, 2 H), 2.93 (m, 2 H), 4.14 (m, 1 H), 7.26 (m, 10 H).

1-(3,4-dimethoxyphenyl)-5-iodo-7-phenylheptane

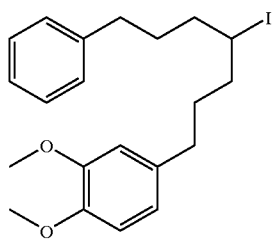

$^1$H NMR (300 MHz, CDCl$_3$): δ 1.72 (m, 4 H), 1.87 (m, 4 H), 2.62 (m, 4 H), 3.88 (s, 3 H), 3.89 (s, 3 H), 4.14 (m, 1 H), 6.73 (m, 2 H), 6.82 (m, 1 H), 7.20 (m, 3 H) 7.28 (m, 2 H).

Triethyl-5-phenyl-2-ph sphonopentanoate

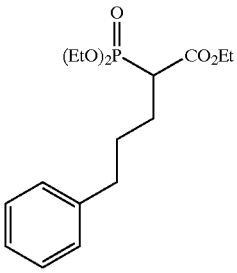

To a suspension of sodium hydride (60% dispersion in mineral oil, 3.07 g, 76.7 mmol) in tetrahydrofuran (250 mL) at 0° C. was added triethylphosphonoacetate (15.0 mL, 75.6 mmol) dropwise. After stirring for 1 h, 1-bromo-3-phenylpropane (8.20 mL, 54.0 mmol) and tetrabutylammonium iodide (0.249 g, 0.674 mmol) were added and the resulting mixture was heated to reflux under nitrogen for 24 h. The reaction was quenched with water and extracted with ethyl acetate. The combined organic extracts were washed with 1N HCl, brine, and dried over magnesium sulfate. The solvent was removed under reduced pressure. The crude product was purified by silica gel chromatography, eluting with ethyl acetate/hexanes (50%), to provide triethyl-5-phenyl-2-phosphonopentanoate (15.1 g, 82%). $^1$H NMR (300 MHz, CDCl$_3$): 1.31 (m, 9 H), 1.70 (m, 2 H), 2.00 (m, 2 H), 2.65 (t, 2 H, J=7.7), 2.97 (ddd, 1 H, J=3.8, 10.9, 22.6), 4.17 (m, 6 H), 7.24 (m, 5 H).

Triethyl-5-(3,4-dimethoxyphenyl)-2-phosphonopentanoate

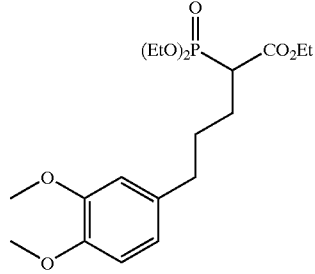

$^1$H NMR (300 MHz, CDC$_{13}$): δ 1.29 (m, 9 H), 1.65 (m, 2 H), 1.97 (m, 2 H), 2.58 (t, 2 H, J=7.5), 2.96 (ddd, 1 H, J=3.9, 10.9, 22.7), 3.86 (s, 3 H), 3.87 (s, 3 H), 4.16 (m, 6 H), 6.74 (m, 3 H).

Triethyl-4-(3,4-dimethoxyphenyl)-2-phosphonobutanoate

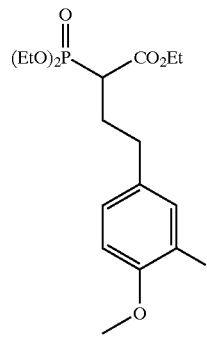

¹H NMR (300 MHz, CDCl₃): δ 1.32 (m, 9 H), 2.14 (m, 1 H), 2.30 (m, 1 H), 2.57 (m, 1 H), 2.70 (m, 1 H), 2.97 (ddd, 1 H, J=3.7, 10.9, 22.9), 3.87 (s, 3 H), 3.89 (s, 3 H), 4.19 (m, 6 H), 6.77 (m, 3 H).
Triethyl-4-phenyl-2-phosphonopentanoate

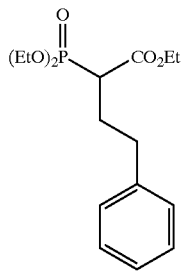

¹H NMR (300 MHz, CDCl₃): δ 1.32 (m, 9 H), 2.20 (m, 2 H), 2.60 (m, 1 H), 2.75 (m, 1 H), 2.98 (ddd, 1 H, J=3.7, 10.9, 22.9), 4.18 (m, 6 H), 7.25 (m, 5 H).
Ethyl-5-phenyl-2-(3-phenylpropyl)-2-pentenoate

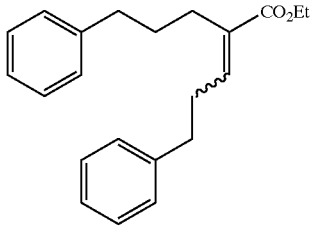

Sodium hydride (60% dispersion in mineral oil, 58.3 mg, 1.46 mmol) was added to a stirred solution of triethyl-5-phenyl-2-phosphonopentanoate (0.426 g, 1.24 mmol) in tetrahydrofuran (8 mL) under nitrogen. After 30 min, hydrocinnamadlehyde (0.210 mL, 1.60 mmol) was added dropwise and stirred at room temperature for 45 min. Water was added and the mixture was extracted with ether. The combined organic extracts were washed with 1N HCl, brine, and dried over magnesium sulfate. The solvent was removed under reduced pressure and the residue was purified by silica gel chromatography, eluting with 3% ethyl acetate/hexanes, to give ethyl-2-(3-phenylpropyl)-5-phenyl-2-pentenoate (0.374 g, 86%). ¹H NMR (300 MHz, CDCl₃): (olefin isomers) δ 1.30 (t, 3 H, J=7.1), 1.72 (m, 2 H), 2.31 (m, 2 H), 2.45 (q, 2 H, J=7.7), 2.63 (m, 2 H), 2.75 (m, 3 H), 4.21 (m, 2 H), 5.90 (m, 0.5 H), 6.82 (m, 0.5 H), 7.25 (m, 10 H).
Ethyl-2-(3-phenylpropyl)-5-(3,4,5-trimethoxyphenyl)-2-pentenoate

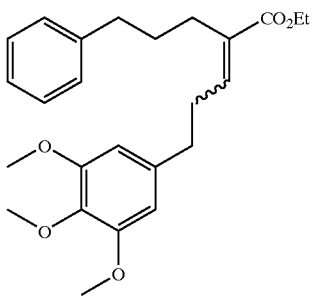

¹H NMR (300 MHz, CDCl₃): (olefin isomers) δ 1.30 (m, 3 H), 1.72 (m, 2 H), 2.32 (q, 2 H, J=7.2), 2.45 (q, 2 H, J=7.6), 2.68 (m, 5 H), 3.85 (m, 9 H), 4.21 (m, 2 H), 5.89 (t, 0.5 H, J=6.9), 6.41 (d, 2 H, J=11.4), 6.81 (t, 0.5 H, J=7.4), 7.23 (m, 5 H).

Ethyl-5-(3,4-dimethoxyphenyl)-2-[3-(3,4-dimethoxyphenyl)propyl]-2-pentenoate

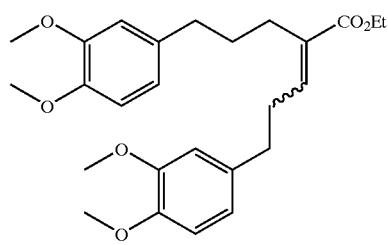

¹H NMR (300 MHz, CDCl₃): (olefin isomers) δ 1.30 (m, 3 H), 1.71 (m, 2 H), 2.30 (q, 2 H, J=7.4), 2.45 (q, 1 H, J=7.6), 2.56 (m, 2 H), 2.72 (m, 3 H), 3.87 (m, 12 H), 5.89 (t, 0.5 H, J=6.6), 6.77 (m, 6.5 H).
Ethyl-3-(3,4-dimethoxyphenyl)-2-[2-(3,4-dimethoxyphenyl)ethyl]-2-propenoate

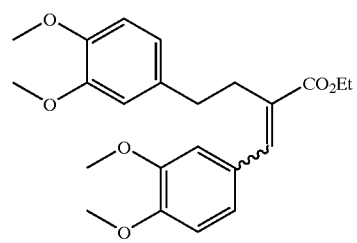

¹H NMR (300 MHz, CDCl₃): δ 1.38 (t, 3 H, J=7.1), 2.86 (m, 4 H), 3.86 (s, 3 H), 3.86 (s, 3 H), 3.87 (s, 3 H), 3.92 (s, 3 H), 4.30 (q, 2 H, J=7.1), 6.87 (m, 6 H), 7.67 (s, 1 H).
Ethyl-2-[2-(3,4-dimethoxyphenyl)ethyl]-4-phenyl-2-butenoate

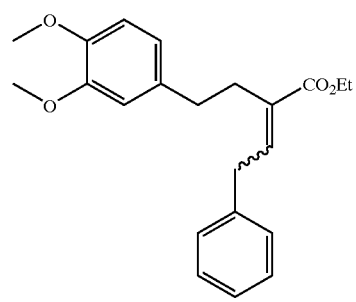

¹H NMR (300 MHz, CDCl₃): (olefin isomers) δ 1.32 (m, 3 H), 1.94 (m, 0.5 H), 2.19 (m, 0.5 H), 2.66 (m, 3 H), 3.20 (m, 0.5 H), 3.39 (d, 0.5 H, J=7.3), 3.87 (m, 6 H), 4.20 (m, 2 H), 6.24 (m, 0.5 H), 6.50 (m, 0.5 H), 6.83 (m, 3 H), 7.25 (m, 5 H).
Ethyl-5-phenyl-2-(3phenylpropyl)pentanoate

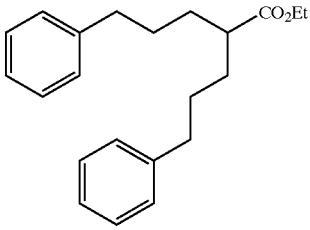

A solution of ethyl-2-(3-phenylpropyl)-5-phenyl-2-pentenoate in methanol (10 mL) was added to a suspension of 10% palladium on carbon (0.112 g) in methylene chloride (10 mL) and the mixture was hydrogenated under 60 psi of hydrogen for 6 h. The catalyst was removed by filtration through a pad of celite and the solvent was removed under reduced pressure to give ethyl-2-(3-phenylpropyl)-5-phenyl-pentanoate (0.787 g, 98%). The crude product was not purified further but used directly in the next step. $^1$H NMR (300 MHz, CDCl$_3$): δ 1.25 (t, 3 H, J=7.1), 1.60 (m, 8 H), 2.39 (m, 1 H), 2.61 (t, 4 H, J=7.3), 4.14 (q, 2 H, J=7.1), 7.24 (m, 10 H).

Ethyl-2-(3phenylpropyl)-5-(3,4,5-trimethoxyphenyl) pentanoate

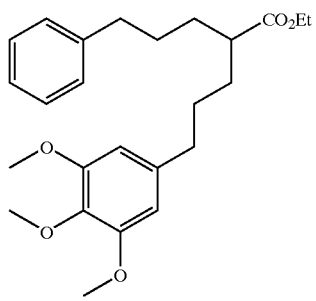

$^1$H NMR (300 MHz, CDCl$_3$): δ 1.26 (t, 3 H, J=7.1), 1.60 (m, 8 H), 2.40 (m, 1 H), 2.56 (t, 2 H, J=7.3), 2.62 (t, 2 H, J=7.3), 3.84 (s, 3 H), 3.86 (s, 6 H), 4.15 (q, 2 H, J=7.1), 6.38 (s, 2 H), 7.24 (m, 5 H).

Ethyl-5-(3,4-dimethoxyphenyl)-2-[3-(3,4-dimethoxyphenyl)propyl]pentanoate

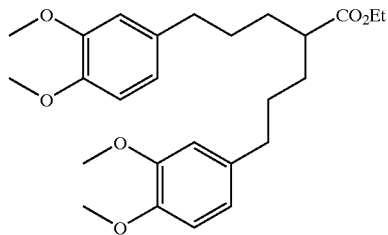

$^1$H NMR (300 MHz, CDCl$_3$): δ 1.26 (t, 3 H, J=7.1), 1.58 (m, 8 H), 2.39 (m, 1 H), 2.56 (t, 1 H, J=7.3), 3.87 (s, 6 H), 3.88 (s, 6 H), 4.15 (q, 2 H, J=7.1), 6.70 (m, 4 H), 6.80 (m, 2 H).

Ethyl-4-(3,4-dimethoxyphenyl)-2-[(3,4-dimethoxyphenyl)methyl]butanoate

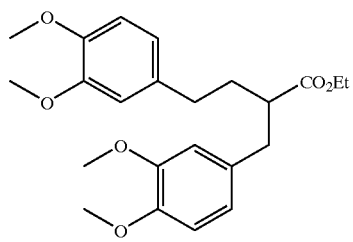

$^1$H NMR (300 MHz, CDCl$_3$): δ 1.21 (t, 3 H, J=7.1), 1.80 (m, 1 H), 1.98 (m, 1 H), 2.62 (m, 4 H), 2.93 (m, 1 H), 3.87 (s, 12 H), 4.11 (q, 2 H, J=7.1), 6.74 (m, 6 H).

Ethyl-4-(3,4-dimethoxyphenyl)-2-(2-phenylethyl)butanoate

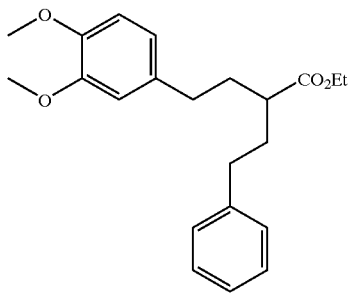

$^1$H NMR (300 MHz, CDCl$_3$): δ 1.32 (t, 3 H, J=7.1), 1.78 (m, 2 H), 2.01 (m, 2 H), 2.54 (m, 5 H), 3.87 (s, 3 H), 3.88 (s, 3 H), 4.20 (q, 2 H, J=7.1), 6.76 (m, 3 H), 7.27 (m, 5 H).

2-(3-Phenylpropyl-5-(3,4,5-trimethoxyphenyl)pentan-1-ol

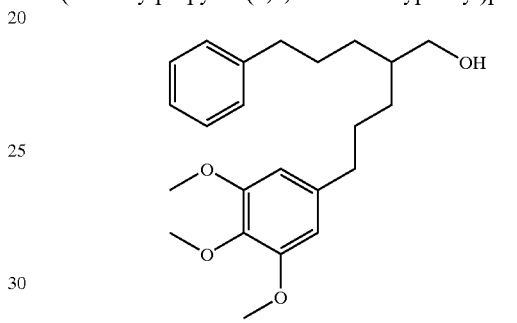

A solution of lithium aluminum hydride (1.0 M in tetrahydrofuran, 2.00 mL, 2.00 mmol) was added dropwise to a solution of ethyl-2-(3-phenylpropyl)-5-(3,4,5-trimethoxyphenyl)pentanoate (1.39 g, 3.36 mmol) in ether (30 mL) at 0° C. After 30 min., a second aliquot of lithium aluminum hydride (1.0 M in tetrahydrofuran, 1.00 mL, 1.00 mmol) was added and the resulting solution was stirred for 30 minutes. Rochelles salt (1 M, 40 mL) was added and the mixture was stirred vigorously for 1.5 h. The aqueous layer was extracted with ether and the combined organic layers were dried over magnesium sulfate and concentrated under reduced pressure. The residue was purified silica gel chromatography, eluting with 50% ethyl acetate/hexanes, to yield 4-hydroxymethyl-7-phenyl-1-(3,4,5-trimethoxyphenyl)heptane (1.23 g, 98%). $^1$H NMR (300 MHz, CDCl$_3$): δ 1.36 (m, 5 H), 1.60 (m, 5 H), 2.56 (t, 2 H, J=7.7), 2.63 (t, 2 H, J=7.7), 3.58 (d, 2 H, J=5.3), 3.84 (s, 3 H), 3.86 (s, 6 H), 6.40 (s, 2 H), 7.25 (m, 5 H).

5-Phenyl-2-(3-phenylpropyl)pentan-1-ol

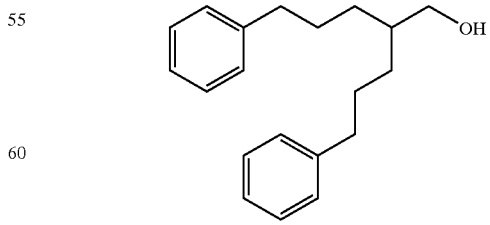

$^1$H NMR (300 MHz, CDCl$_3$): δ 1.40 (m, 4 H), 1.61 (m, 5 H), 2.62 (t, 4 H, J=7.7), 3.56 (d, 2 H, J=5.4), 7.25 (m, 10 H).

5-(3,4-dimethoxyphenyl)-2-[3-(3,4-dimethoxyphenyl)propyl]pentan-1-ol

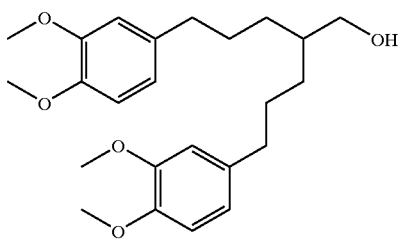

¹H NMR (300 MHz, CDCl₃): δ 1.40 (m, 5 H), 1.60 (m, 5 H), 2.57 (t, 4 H, J=7.6), 3.57 (d, 2 H, J=5.4), 3.87 (s, 6 H), 3.89 (s, 6 H), 6.72 (m, 4 H), 6.80 (m, 2 H).

4-(3,4-Dimethoxyphenyl)-2-[(3,4-dimethoxyphenyl)methyl]butan-1-ol

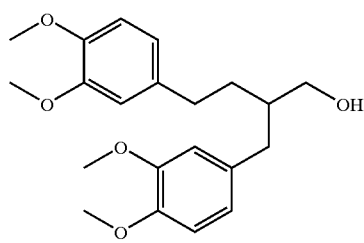

¹H NMR (300 MHz, CDCl₃): δ 1.75 (m, 3 H), 2.64 (m, 4 H), 3.61 (d, 2 H, J=5.3), 3.87 (s, 6 H), 3.88 (s, 6 H), 6.75 (m, 6 H).

4-(3,4-Dimethoxyphenyl)-2-(2-phenylethyl)butan-1-ol

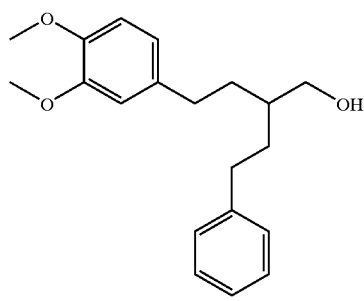

¹H NMR (300 MHz, CDCl₃): δ 1.40 (bs, 1 H), 1.70 (m, 5 H), 2.65 (m, 4 H), 3.68 (d, 2 H, J=5.0), 3.88 (s, 3 H), 3.89 (s, 3 H), 6.77 (m, 3 H), 7.26 (m, 5 H).

4-Bromomethyl-1,7-diphenylheptane

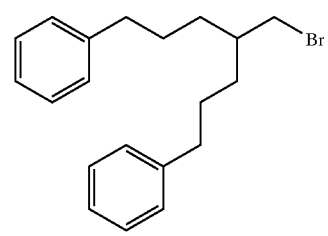

A solution of triphenylphosphine (0.885 g, 3.37 mmol) in methylene chloride (5 mL) was added to a solution of yield 1,7-diphenyl-4-hydroxymethylheptane (0.666 g, 2.36 mmol) and carbon tetrabromide (1.10 g, 3.33 mmol) in methylene chloride (10 mL) at 0° C. under nitrogen. After 16 h, the solvent was removed under reduced pressure and the residue was purified by silica gel chromatography, eluting with methylene chloride/hexanes (5% to 10%) to provide 4-bromomethyl-1,7-diphenylheptane (0.723 g, o9%). ¹H NMR (300 MHz, CDCl₃): δ 1.45 (m, 4 H), 1.63 (m, 5 H), 2.62 (t, 4 H, J=7.6), 3.46 (d, 2 H, J=4.7), 7.25 (m, 10 H).

4-Bromomethyl-7-phenyl-1-(3,4,5-trimethoxyphenyl)heptane

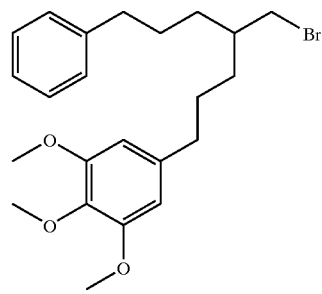

¹H NMR (300 MHz, CDCl₃): δ 1.45 (m, 4 H), 1.62 (m, 5 H), 2.57 (t, 2 H, J=7.5), 2.63 (t, 2 H, J=7.6), 3.48 (d, 2 H, J=4.6), 3.85 (s, 3 H), 3.87 (s, 6 H), 6.41 (s, 2 H), 7.25 (m, 5 H).

1,7-Bis(3,4-dimethoxyphenyl)-3-bromomethylbutane

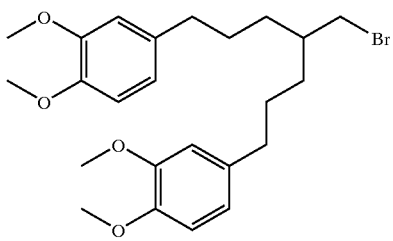

¹H NMR (300 MHz, CDCl₃): δ 1.55 (m, 9 H), 2.57 (t, 4 H, J=7.5), 3.47 (d, 2 H, J=4.6), 3.88 (s, 6 H), 3.89 (s, 6 H), 6.77 (m, 6 H).

1,4-Bis(3,4-dimethoxyphenyl)-3-bromomethylbutane

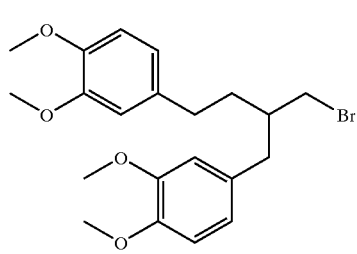

¹H NMR (300 MHz, CDCl₃): δ 1.82 (m, 3 H), 2.67 (m, 4 H), 3.44 (m, 2 H), 3.88 (s, 6 H), 3.89 (s, 6 H), 6.77 (m, 6 H).

4-Bromomethyl-(3,4-Dimethoxyphenyl)-5-phenylpentane

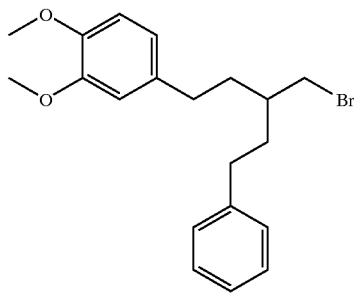

¹H NMR (300 MHz, CDCl₃): δ 1.77 (m, 5 H), 2.61 (m, 4 H), 3.57 (d, 2 H, J=3.4), 3.88 (s, 3 H), 3.89 (s, 3 H), 6.73 (m, 2 H), , 6.80 (m, 1 H), 7.21 (m, 3 H), 7.31 (m, 2 H).

(S)-5-oxoproline methyl ester

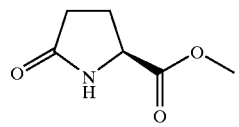

To a solution of L-pyroglutamic acid (32.7 g, 0.253 mol) in methanol (600 mL) was added thionyl chloride (2.40 mL, 32.9 mmol), and the resulting solution was stirred at room temperature for 16 h. The reaction mixture was neutralized to pH=7 with saturated aqueous sodium bicarbonate and concentrated in vacuo. The residue was dissolved in methylene chloride, washed with brine, dried over magnesium sulfate, and concentrated. The residue was distilled under high vacuum to give the product as a colorless oil (28.9 g, 80%), b.p. 118–126° C./0.35 mm Hg. ¹H NMR (300 MHz, CDCl₃): δ 2.36 (m, 4 H), 3.77 (s, 3 H), 4.27 (dd, 1 H, J=5.0, 8.4), 6.78 (s, 1 H).

(S)-1-Benzyl-5-oxoproline methyl ester

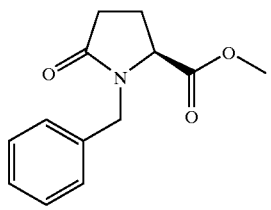

To a suspension of sodium hydride (60% dispersion in mineral oil washed with hexanes, 12.2 g, 0.305 mol) in tetrahydrofuran (600 mL) was added dropwise a solution (S)-1-benzyl-5-oxoproline methyl ester (29.0 g, 0.203 mol) and benzyl bromide (27.0 mL, 0.227 mol) in tetrahydrofuran (200 mL) at 0° C. under nitrogen. The resulting mixture was warmed slowly to room temperature, stirred for 14 h, and the washed with saturated aqueous sodium bicarbonate and brine. The combined aqueous layers were back extracted with ether and the combined organic layer were dried over magnesium sulfate, and concentrated. The residue was purified by silica gel chromatography, eluting with 60% ethyl acetate/hexanes, to produce the product (36.5 g, 77%). ¹H NMR (300 MHz, CDCl₃): δ 2.09 (m, 1 H), 2.27 (m, 1 H), 2.44 (m, 1 H), 2.58 (m, 1 H), 3.69 (s, 3 H), 4.00 (m, 2 H), 5.03 (d, 1 H, J=14.8), 7.29 (m, 5 H).

(S)-1-Benzyl-5-thiooxoproline methyl ester

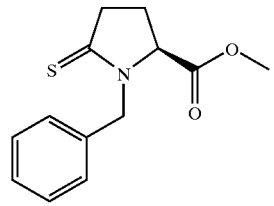

To a solution (S)-1-benzyl-5-oxoproline methyl ester (10.1 g, 43.4 mmol) in tetrahydrofuran (100 mL) Lawessons reagent (13.2 g, 32.6 mmol) at room temperature under nitrogen. The reaction was stirred for 1 h and then concentrated. The residue was dissolved in ethyl acetate, washed with saturated aqueous sodium bicarbonate, and brine. Removal of the organic phase under reduced pressure afforded the crude product (9.75 g, 90%). The crude product was not purified further but used directly in the next step. ¹H NMR (300 MHz, CDCl₃): δ 2.18 (m, 2 H), 3.16 (m, 2 H), 3.70 (s, 3 H), 4.32 (dd, 1 H, J=3.2, 9.3), 4.39 (d, 1 H, J=14.6), 5.75 (d, 1 H, J=14.6), 7.33 (m, 5 H).

(S)-1-Benzyl-2-thiomethoxy-5-methoxycarbonyl-1-pyrrolinium iodide

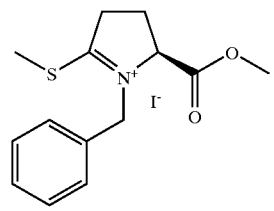

A solution of (S)-1-benzyl-5-thiooxoproline methyl ester (9.75 g, 39.1 mmol) and methyl iodide (12.5 mL, 0.201 mol) was stirred at room temperature under nitrogen for 2 h. The excess methyl iodide was removed in vacuo and the residue was triturated with benzene. The resulting yellow solid was collected by filtration and washed with benzene and ether to give the desired compound (15.2 g, 99%). ¹H NMR (300 MHz, CDCl₃): δ 2.28 (m, 1 H), 3.07 (s, 3 H), 3.10 (m, 1 H), 3.39 (m, 1 H), 3.64 (s, 3 H), 4.24 (m, 1 H), 4.74 (d, 1 H, J=14.7), 4.90 (dd, 1 H, J=3.0, 10.1), 5.13 (d, 1 H, J=14.7), 7.40 (m, 5 H).

(S)-1-Benzyl-5-nitromethylene proline methyl ester

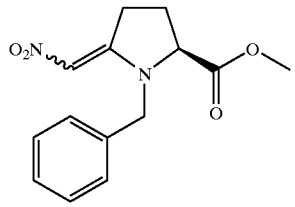

To a stirred solution of (S)-1-benzyl-2-thiomethoxy-5-methoxycarbonyl-1-pyrrolinium iodide (38.4 g, 99.8 mmol) in dimethylformamide (200 mL) under nitrogen were added triethylamine (16.4 mL, 0.118 mol) and nitromethane (27.0 mL, 0.498 mol). The reaction was stirred for 16 h and then concentrated under reduced pressure. Purification by silica gel chromatography, eluting with 40% ethyl acetate/hexanes produced the desired nitroenamine (13.9 g, 50%). ¹H NMR (300 MHz, CDCl₃): δ 2.31 (m, 3 H), 3.40 (m, 1 H), 3.73 (s, 3 H), 4.26 (dd, 1 H, J=3.0, 9.3), 4.32 (d, 1 H, J=15.6), 4.53 (d, 1 H, J=15.6), 6.89 (s, 1 H), 7.29 (m, 5 H).

(1S,5R)-8-Benzyl-3,8-diazabicyclo[3.2.1]octan-2-one

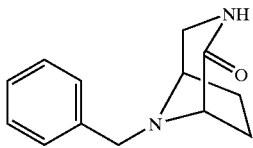

(S)-1-Benzyl-5-nitromethylene proline methyl ester (3.22 g, 11.6 mmol) was added to a suspension of 10% palladium on carbon (1.35 g) in methanol (75 mL) and the mixture was hydrogenated under 30 psi of hydrogen for 20 h. The catalyst was removed by filtration through a pad of celite and the solvent was removed under reduced pressure. The crude product was purified by silica gel chromatography, eluting with 5% methanol/methylene chloride, to yield the desired product (1.49 g, 60%). $^1$H NMR (300 MHz, CDCl$_3$): δ 1.78 (m, 1 H), 2.08 (m, 1 H), 2.22 (m, 2 H), 2.99 (dd, 1 H, J=2.0, 11.3), 3.38 (m, 1 H), 3.49 (d, 1 H, J=6.1), 3.67 (dd, 1 H, J=3.9, 11.3), 3.78 (s, 2 H), 5.66 (s, 1 H), 7.33 (m, 5 H). MS ESI$^+$: m/z 217 (M+H)$^+$.

Methyl-1-t-butoxycarbonyl-6-oxo-2-piperidinecarboxylate

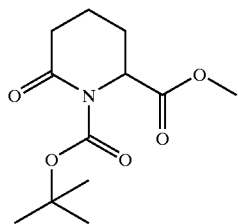

Sodium periodate (32.0 g, 150 mmol) and ruthenium(IV) oxide (0.290 g, 2.18 mmol) were added to a suspension of methyl-N-t-butoxycarbonyl pipecolinate (12.5 g, 51.5 mmol) in acetonitrile (30 mL) and water (150 mL) at room temperature. The mixture was stirred for 18 h, extracted with ethyl acetate, and treated with isopropyl alcohol for 2 h. The suspension was filtered through celite and the organic layer was washed with brine and dried over magnesium sulfate. The solvent was removed under reduced pressure and the residue was purified by silica gel chromatography, eluting with 50% ethyl acetate/hexanes, to afford the product as a light yellow oil (9.06 g, 68%). $^1$H NMR (300 MHz, CDCl$_3$): δ 1.49 (s, 9 H), 1.75 (m, 2 H), 2.09 (m, 2 H), 2.50 (m, 2 H), 3.76 (s, 3 H), 4.70 (m, 1 H).

Methyl-1-t-butoxycarbonyl-6-cyano-piperidine carboxylate

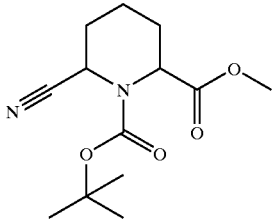

A solution of lithium triethylborohydride (1.0 M in tetrahydrofuran, 60.0 mL, 60.0 mmol) was added dropwise to a solution of methyl-1-t-butoxycarbonyl-6-oxo-2-piperidinecarboxylate (10.3 g, 40.0 mmol) in tetrahydrofuran (150 mL) at −78° C. under nitrogen. The reaction was stirred for 20 min., treated with methanol (20 mL), and warmed to 0° C. Saturated aqueous sodium bicarbonate (100 mL) and hydrogen peroxide (30%, 20 mL) were added and the resulting mixture was stirred for 20 min. The solvent was removed under reduced pressure and the residue was extracted with methylene chloride. The combined organics were washed with saturated aqueous sodium bicarbonate, brine, dried over sodium sulfate, and concentrated. The crude product was dissolved in methanol (100 mL) and cooled to −10° C. The reaction was treated with p-toluenesulfonic acid until the pH=1 and then stirred for 10 min. Saturated aqueous sodium bicarbonate was added until the pH=7 and the solvent removed under reduced pressure. The residue was extracted with methylene chloride and the combined organic layers were washed with saturated aqueous sodium bicarbonate, brine, and dried over sodium sulfate. The solvent was concentrated to ~150 mL at room temperature. The solution was cooled to −78° C. and trimethylsilyl cyanide (21.3 mL, 0.160 mol) was added followed by boron trifluoride diethyl etherate (1.52 mL, 12.0 mmol). The reaction was stirred at −78° C. for 2 h and then −55° C. for 1 h. The mixture was treated with saturated aqueous sodium bicarbonate and extracted with methylene chloride. The combined organic layers were washed with saturated aqueous sodium bicarbonate, brine and dried over sodium sulfate. The solvent was removed under reduced pressure and the residue was purified by silica gel chromatography, eluting with ethyl acetate/hexanes (10% to 25%), to produce the desired product (8.00 g, 74%). $^1$H NMR (300 MHz, CDCl$_3$): δ 1.45 (s, 9 H), 1.72 (m, 3 H), 2.12 (m, 2 H), 2.40 (d, 1 H, J=8.1), 3.71 (m, 3 H), 4.94 (m, 2 H).

9-t-butoxycarbonyl-3,9-diazabicyclo[3.3.1]nonan-2-one

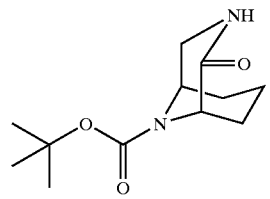

A solution of methyl-1-t-butoxycarbonyl-6-cyano-piperidine carboxylate (2.28 g, 10.5 mmol) in methanol (30 mL) was added to a suspension of platinium(IV) oxide (0.508 g) in CHCl$_3$ (30 mL) and the mixture was hydrogenated under 60 psi of hydrogen for 18 h. The catalyst was removed by filtration through a pad of celite and the solvent was removed under reduced pressure. The residue was dissolved in tetrahydrofuran (50 mL) and triethylamine (10 mL) was added and the mixture heated to reflux under nitrogen for 20 h. The solvent was removed under reduced pressure and the crude product was purified by silica gel chromatography, eluting with 5% methanol/methylene chloride, to provide the desired product (1.54, 61%). $^1$H NMR (300 MHz, CDCl$_3$): δ 1.48 (s, 9 H), 1.79 (m, 5 H), 1.97 (d, 1 H, J=10.3), 3.22 (dd, 1 H, J=3.0, 11.9), 3.75 (m, 1 H), 4.50 (m, 2 H), 6.30 (s, 1 H).

(1S,5R)-8-Benzyl-3,8-diaza-3-(3-phenylpropyl)bicyclo[3.2.1]octan-2-one

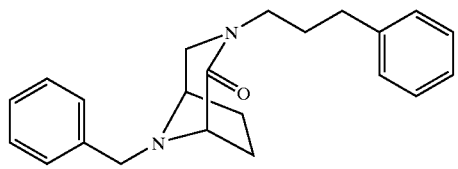

To a solution of (1S,5R)-8-Benzyl-3,8-diazabicyclo[3.2.1]octan-2-one (98.4 mg, 0.455 mmol) in tetrahydrofuran (5 mL) was added sodium hydride (60% dispersion in mineral oil, 37.3 mg, 0.932 mmol). After 30 min., 3-bromo-1-phenylpropane (90 μL, 0.592 mmol) was added and the reaction was heated to reflux under nitrogen for 16 h. The mixture was treated with water and extracted with methylene chloride. The combined organic layers were dried over magnesium sulfate, concentrated, and purified by silica gel chromatography, eluting with 60% ethyl acetate/hexanes, to afford the product (0.128 g, 84%). $^1$H NMR (300 MHz, CDCl$_3$): δ 1.68 (m, 1 H), 1.94 (m, 3 H), 2.21 (m, 2 H), 2.67 (m, 2 H), 2.86 (d 1 H, J=11.4), 3.27 (m, 1 H), 3.48 (m, 1 H), 3.55 (m, 3 H), 3.71 (s, 2 H), 7.28 (m, 10 H). MS ESI$^+$: m/z 335 (M+H)$^+$.

(1S,5R)-8-Benzyl-3,8-diaza-3-(4-phenylbutyl)bicyclo[3.2.1]octan-2-one

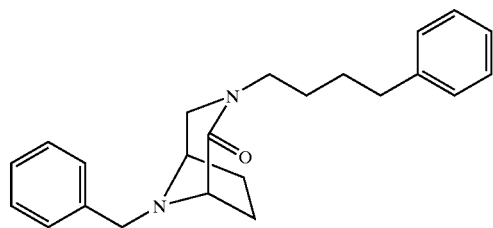

$^1$H NMR (300 MHz, CDCl$_3$): δ 1.66 (m, 5 H), 2.00 (m, 1 H), 2.20 (m, 2 H), 2.68 (t, 2 H, J=7.1), 2.82 (d, 1 H, J=11.3), 3.26 (m, 1 H), 3.38 (m, 1 H), 3.44 (m, 1 H), 3.54 (m, 2 H), 3.70 (s, 2 H), 7.27 (m, 10 H).

(1S,5R)-8-Benzyl-3,8-diaza-3-[3-(3,4,5-trimethoxyphenyl)propyl]bicyclo[3.2.1]octan-2-one

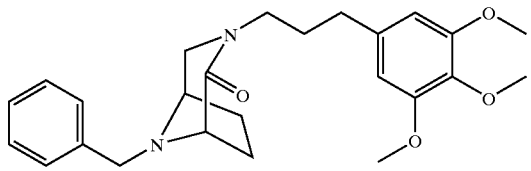

$^1$H NMR (300 MHz, CDCl$_3$): δ 1.66 (m, 1 H), 1.89 (m, 2 H), 2.01 (m, 1 H), 2.22 (m, 2 H), 2.61 (t, 2 H, J=7.8), 2.88 (d, 1 H, J=11.5), 3.43 (m, 5 H), 3.72 (s, 2 H), 3.85 (s, 3 H), 3.88 (s, 6 H), 6.45 (s, 2 H), 7.31 (m, 5 H).

(1S,5R)-8-Benzyl-3,8-diaza-3-[2-(3,4-dimethoxyphenyl)ethyl]bicyclo[3.2.1]octan-2-one

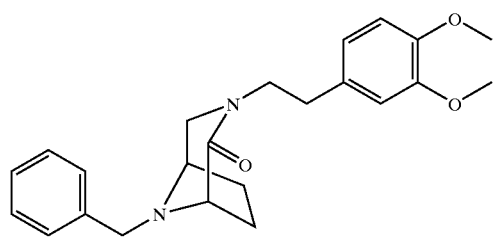

$^1$H NMR (300 MHz, CDCl$_3$): δ 1.49 (m, 1 H), 1.93 (m, 1 H), 2.15 (m, 2 H), 2.69 (d, 1 H, J=11.4), 2.88 (m, 2 H), 3.30 (m, 1 H), 3.45 (m, 3 H), 3.64 (s, 2 H), 3.74 (m, 1 H), 3.87 (s, 3 H), 3.90 (s, 3 H), 6.81 (m, 3 H), 7.29 (m, 5 H).

(1S,5R)-8-Benzyl-3,8-diaza-3-[3-(3,4-dimethoxyphenyl)propyl]bicyclo[3.2.1]-octan-2-one

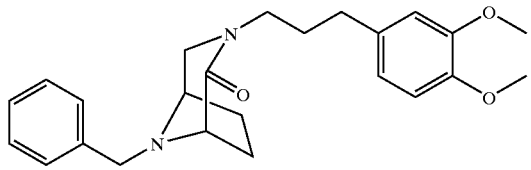

$^1$H NMR (300 MHz, CDCl$_3$): δ 1.68 (m, 1 H), 1.88 (m, 2 H), 2.01 (m, 1 H), 2.22 (m, 2 H), 2.61 (t, 2 H, J=7.8), 2.87 (d, 1 H, J=11.5), 3.28 (m, 1 H), 3.52 (m, 4 H), 3.73 (s, 2 H), 3.87 (s, 3 H), 3.90 (s, 3 H), 6.79 (m, 3 H), 7.33 (m, 5 H).

(1S,5R)-8-Benzyl-3,8-diaza-3-[4-(3,4-dimethoxyphenyl)butyl]bicyclo[3.2.1]octan-2-one

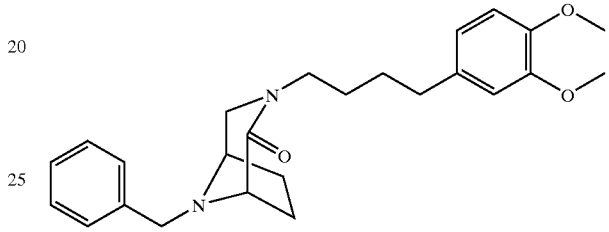

$^1$H NMR (300 MHz, CDCl$_3$): δ 1.62 (m, 5 H), 2.02 (m, 1 H), 2.22 (m, 2 H), 2.62 (t, 1 H, J=7.1), 2.84 (d, 1 H, J=11.3), 3.28 (m, 1 H), 3.43 (m, 2 H), 3.55 (m, 2 H), 3.72 (m, 2 H), 3.87 (s, 3 H), 3.88 (s, 3 H), 6.78 (m, 3 H), 7.32 (m, 5 H).

(1S,5R)-8-Benzyl-3,8-diaza-3-[3-(1,1,2,2-tetramethyl-1-silapropoxy]bicyclo[3.2.1]octan-2-one

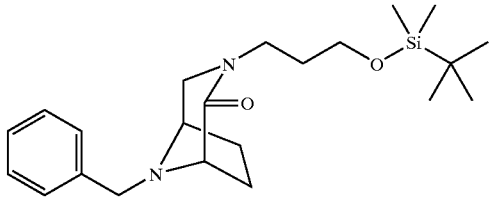

$^1$H NMR (300 MHz, CDCl$_3$): δ 0.08 (s, 6 H), 0.91 (s, 9 H), 1.69 (m, 1 H), 1.80 (m, 2 H), 2.00 (m, 1 H), 2.21 (m, 2 H), 2.91 (d, 1 H, J=11.5), 3.29 (m, 1 H), 3.39 (m, 1 H), 3.49 (m, 2 H), 3.65 (m, 5 H), 7.32 (m, 5 H).

(1S,5R)-8-Benzyl-3,8-diaza-3-[3-phenyl-1-(2-phenylethyl)propyl]bicyclo[3.2.1]octan-2-one

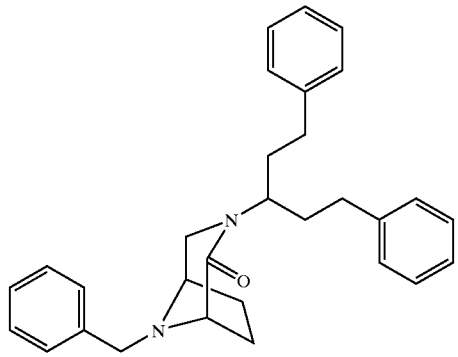

¹H NMR (300 MHz, CDCl₃): δ 1.80 (m, 5 H), 2.09 (m, 1 H), 2.27 (m, 2 H), 2.60 (m, 4 H), 2.81 (m, 1 H), 3.50 (d, 2 H, J=7.9), 3.67 (d, 1 H, J=5.4), 3.79 (s, 2 H), 4.75 (bs, 1 H), 7.29 (m, 15 H). MS ESI⁺: m/z 439 (M+H)⁺.

(1S,5R)-8-Benzyl-3,8-diaza-3-[4-(3,4-dimethoxyphenyl)-1-(3-phenylpropyl)butyl]bicyclo[3.2.1]octan-2-one

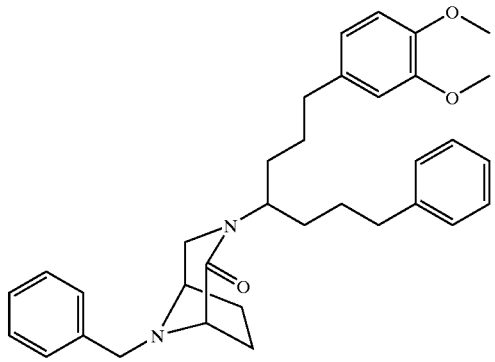

¹H NMR (300 MHz, CDCl₃): δ 1.57 (m, 9 H), 1.99 (m, 1 H), 2.20 (m, 2 H), 2.62 (m, 5 H), 3.25 (m, 1 H), 3.38 (m, 1 H), 3.58 (d, 1 H, J=5.7), 3.71 (s, 2 H), 3.87 (s, 6 H), 4.69 (m, 1 H), 6.75 (m, 3 H), 7.24 (m, 10 H).

(1S,5R)-8-Benzyl-3,8-diaza-3-[2-(3-phenylpropyl)-5-(3,4,5-trimethoxyphenyl)pentyl]bicyclo[3.2.1]octan-2-one

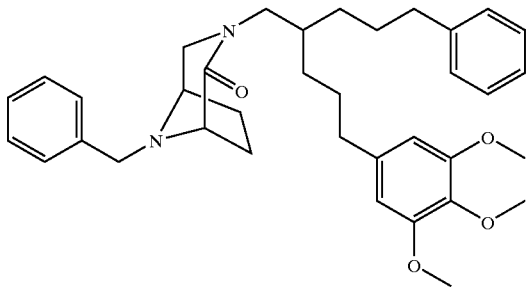

To a solution of (1S,5R)-8-benzyl-3,8-diazabicyclo[3.2.1]octan-2-one (0.199 g, 0.921 mmol) in tetrahydrofuran (6 mL) was added sodium hydride (60% dispersion in mineral oil, 59.5 mg, 1.49 mmol). After 30 min., 4-bromomethyl-7-phenyl-1-(3,4,5-trimethoxyphenyl)heptane (0.531 g, 1.22 mmol) in tetrahydrofuran (4 mL) and tetrabutylammonium iodide (31.6 mg, 0.0855 mmol) were added and the reaction was heated to reflux under nitrogen for 16 h. The mixture was treated with water and extracted with ethyl acetate. The combined organic layers were dried over magnesium sulfate, concentrated, and purified by silica gel chromatography, eluting with 65% ethyl acetate/hexanes, to afford the product (0.368 g, 70%). ¹H NMR (300 MHz, CDCl₃): δ 1.36 (m, 4 H), 1.69 (m, 7 H), 2.15 (m, 2 H), 2.58 (m, 4 H), 2.77 (d, 1 H, J=11.4), 2.96 (m, 1 H), 3.32 (m, 1 H), 3.54 (m, 3 H), 3.66 (s, 2 H), 3.84 (m, 9 H), 6.40 (s, 2 H), 7.26 (m, 10 H). MS ESI⁺: m/z 571 (M+H)⁺.

(1S,5R)-8-Benzyl-3,8-diaza-3-[5-phenyl-2-(3-phenylpropyl)pentyl]bicyclo[3.2.1]octan-2-one

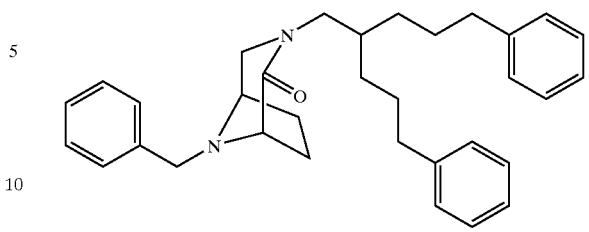

¹H NMR (300 MHz, CDCl₃): δ 1.35 (m, 4 H), 1.62 (m, 6 H), 1.88 (m, 1 H), 2.15 (m, 2 H), 2.60 (m, 4 H), 2.76 (d, 1 H, J=11.4), 2.96 (dd, 1 H, J=6.9, 13.4), 3.32 (m, 1 H), 3.43 (dd, 1 H, J=3.9, 11.4), 3.52 (q, 2 H, J=7.2), 3.66 (s, 2 H), 7.25 (m, 15 H). MS ESI⁺: m/z 481 (M+H)⁺.

(1S,5R)-8-Benzyl-3,8-diaza-3-[5-(3,4-dimethoxyphenyl)-2-(3-(3,4-dimethoxyphenyl)propyl)pentyl]bicyclo[3.2.1]octan-2-one

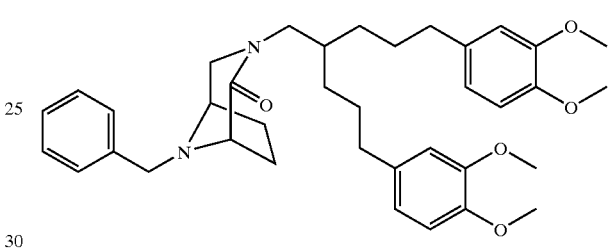

MS ESI⁺: m/z 601 (M+H)⁺.

(1S,5R)-8-Benzyl-3,8-diaza-3-[4-(3,4-dimethoxyphenyl)-2-((3,4-dimethoxyphenyl)methyl)butyl]bicyclo[3.2.1]octan-2-one

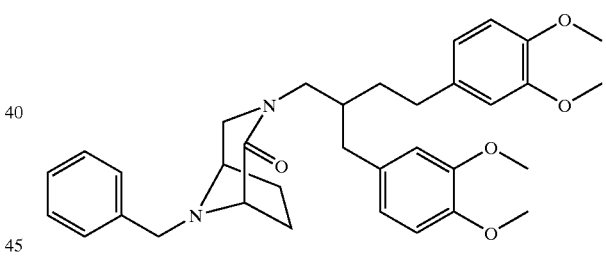

¹H NMR (300 MHz, CDCl₃): δ 1.54 (m, 4 H), 1.99 (m, 2 H), 2.18 (m, 2 H), 2.63 (m, 5 H), 3.36 (m, 2 H), 3.50 (m, 2 H), 3.72 (m, 2 H), 3.84 (m, 12 H), 6.74 (m, 6 H), 7.30 (m, 5 H). MS ESI⁺: m/z 559 (M+H)⁺.

(1S,5R)-8-Benzyl-3,8-diaza-3-[4-(3,4-dimethoxyphenyl)-2-(2-phenylethyl)butyl]bicyclo[3.2.1]octan-2-one

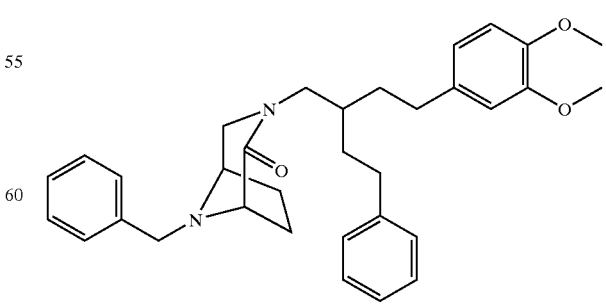

¹H NMR (300 MHz, CDCl₃): δ 1.66 (m, 6 H), 1.97 (m, 1 H), 2.17 (m, 2 H), 2.63 (m, 5 H), 3.14 (m, 1 H), 3.40 (m,

2 H), 3.61 (m, 4 H), 3.87 (m, 6 H), 6.73 (m, 3 H), 7.23 (m, 10 H). MS ESI+: m/z 513 (M+H)+.

(1S,5R)-8-benzyl-3,8-diaza-3-(3-hydroxypropyl)bicyclo[3.2.1]octan-2-one

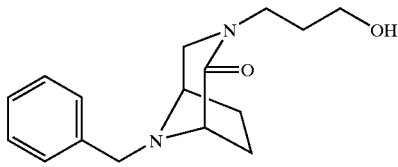

Tetrabutylammonium fluoride (1.0M in tetrahydrofuran, 0.950 mL, 0.950 mmol) was added to a solution of (1S,5R)-8-benzyl-3,8-diaza-3-[(3-propoxy)-t-butyldimethylsilyl]bicyclo-[3.2.1]octan-2-one (0.278 g, 0.716 mmol) in tetrahydrofuran (7 mL) and the resulting solution was stirred for 30 min. The mixture was treated with water and extracted with methylene chloride. The combined organic layers were washed with brine, dried over magnesium sulfate, and concentrated. Purification by silica gel chromatography, eluting with 5% methanol/methylene chloride gave the product (0.194 g, 99%). $^1$H NMR (300 MHz, CDCl$_3$): δ 1.70 (m, 3 H), 2.02 (m, 1 H), 2.25 (m, 2 H), 2.87 (d, 1 H, J=11.5), 3.30 (m, 1 H), 3.62 (m, 8 H), 3.94 (m, 1 H), 7.32 (m, 5 H).

(1S,5R)-8-Benzyl-3,8-diaza-3-(3-(3-pyridyloxy)propyl)bicyclo[3.2.1]octan-2-one

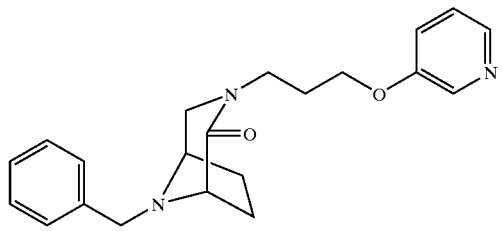

To a solution of (1S,5R)-8-benzyl-3,8-diaza-3-(3-propoxy)bicyclo-[3.2.1]octan-2-one (0.104 g, 0.378 mmol), 3-hydroxypyridine (50.5 mg, 0.531 mmol), and triphenylphosphine (0.135 g, 0.515 mmol) was added diisopropylazodicarboxylate (0.100 mL, 0.508 mmol) at room temperature under nitrogen. After 16 h, the solvent was evaporated and the residue was purified by silica gel chromatography, eluting with 2% methanol/methylene chloride to provide the desired compound (62.6 mg, 47%). $^1$H NMR (300 MHz, CDCl$_3$): δ 1.70 (m, 1 H), 2.11 (m, 5 H), 2.94 (d, 1 H, J=11.4), 3.42 (m, 3 H), 3.67 (m, 4 H), 4.06 (m, 2 H), 7.30 (m, 7 H), 8.28 (m, 2 H).

9-t-Butoxycarbonyl-3,9-diaza-3-[3-(3,4,5-trimethoxyphenyl)propyl]bicyclo[3.3.1]nonan-2-one

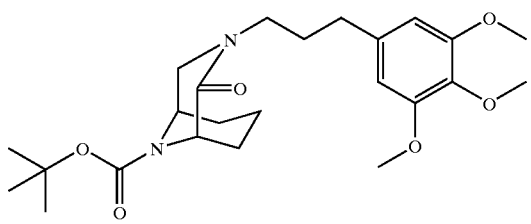

To a solution of 9-t-butoxycarbonyl-3,9-diazabicyclo[3.3.1]nonan-2-one (0.120 g, 0.501 mmol) in tetrahydrofuran (5 mL) was added sodium hydride (60% dispersion in mineral oil, 42.6 mg, 1.06 mmol). After 30 min., a solution of 3-bromo-1-(3,4,5-trimethoxyphenyl)propane (0.188 g, 0.651 mmol) in tetrahydrofuran (3 mL) was added and the reaction was heated to reflux under nitrogen for 16 h. The mixture was treated with water and extracted with methylene chloride. The combined organic layers were dried over magnesium sulfate, concentrated, and purified by silica gel chromatography, eluting with 50% ethyl acetate/hexanes, to afford the product (0.189 g, 84%). $^1$H NMR (300 MHz, CDCl$_3$): δ 1.46 (s, 9 H), 1.67 (m, 5 H), 1.88 (m, 4 H), 2.58 (m, 2 H), 3.09 (d, 1 H, J=12.1), 3.30 (m, 1 H), 3.56 (m, 1 H), 3.71 (m, 1 H), 3.82 (s, 3 H), 3.85 (s, 6 H), 4.55 (m, 1 H), 6.42 (s, 2 H).

9-t-Butoxycarbonyl-3,9-diaza-3-(3-phenylpropyl)bicyclo[3.3.1]nonan-2-one

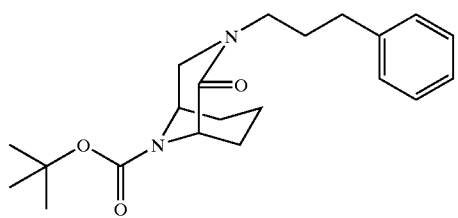

$^1$H NMR (300 MHz, CDCl$_3$): δ 1.47 (s, 9 H), 1.71 (m, 4 H), 1.88 (m, 4 H), 2.66 (m, 2 H), 3.08 (d, 1 H, J=12.1), 3.27 (m, 1 H), 3.66 (m, 2 H), 4.55 (m, 2 H), 7.26 (m, 5 H).

9-t-Butoxycarbonyl-3,9-diaza-3-(4-phenylbutyl)bicyclo[3.3.1]nonan-2-one

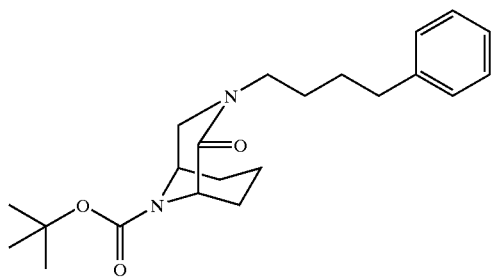

$^1$H NMR (300 MHz, CDCl$_3$): δ 1.47 (s, 9 H), 1.63 (m, 8 H), 1.81 (m, 1 H), 1.98 (m,1 H), 2.67 (m, 2 H), 3.06 (d, 1 H, J=12.1), 3.31 (m, 1 H), 3.54 (m, 1 H), 3.68 (m, 1 H), 4.54 (m, 2 H), 7.25 (m, 5 H).

9-t-Butoxycarbonyl-3,9-diaza-3-(5-phenylpentyl)bicyclo[3.3.1]nonan-2-one

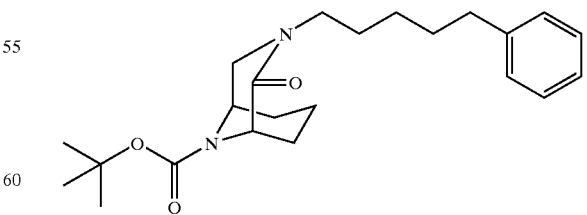

$^1$H NMR (300 MHz, CDCl$_3$): δ 1.38 (m, 2 H), 1.48 (s, 9 H), 1.66 (m, 8 H), 1.81 (m, 1 H), 1.96 (m, 1 H), 2.63 (t, 2 H, J=7.6), 3.07 (d, 1 H, J=12.1), 3.20 (m, 1 H), 3.55 (m, 1 H), 3.68 (m, 1 H), 4.54 (m, 2 H), 7.24 (m, 5 H).

9-t-Butoxycarbonyl-3,9-diaza-3-[3-(3,4-dimethoxyphenyl)propyl]bicyclo[3.3.1]nonan-2-one

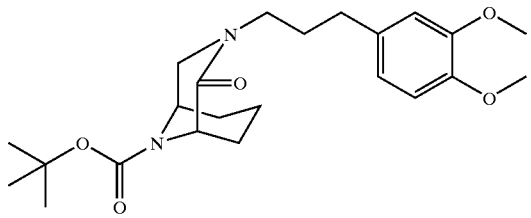

¹H NMR (300 MHz, CDCl₃): δ 1.48 (s, 9 H), 1.67 (m, 4 H), 1.92 (m, 4 H), 2.61 (m, 2 H), 3.09 (d, 1 H, J=12.1), 3.30 (m, 1 H), 3.59 (m, 1 H), 3.71 (m, 1 H), 3.87 (s, 3 H), 3.90 (s, 3 H), 4.56 (m, 2 H), 6.78 (m, 3 H).

9-t-Butoxycarbonyl-3,9-diaza-3-[4-(3,4-dimethoxyphenyl)butyl]bicyclo[3.3.1]nonan-2-one

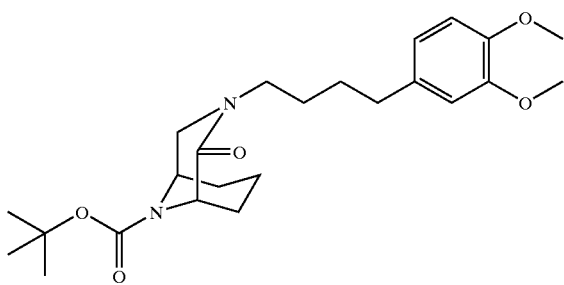

¹H NMR (300 MHz, CDCl₃): δ 1.47 (s, 9 H), 1.66 (m, 8 H), 1.81 (m, 1 H), 1.98 (m, 1 H), 2.62 (m, 2 H), 3.07 (d, 1 H, J=12.1), 3.30 (m, 1 H), 3.55 (m, 1 H), 3.69 (m, 1 H), 3.87 (s, 3 H), 3.89 (s, 3 H), 4.55 (m, 2 H), 6.77 (m, 3 H).

9-t-Butoxycarbonyl-3,9-diaza-3-[4-(3,4-dimethoxyphenyl)-1-(3-phenylpropyl)butyl]bicyclo[3.3.1]-nonan-2-one

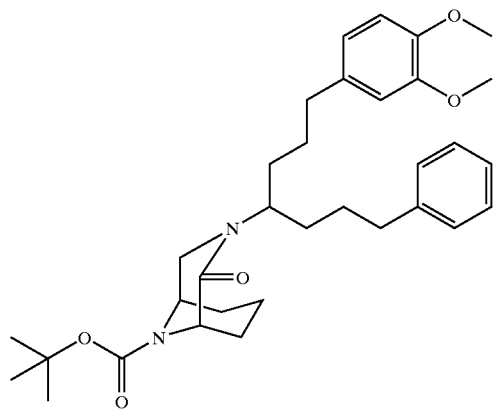

¹H NMR (300 MHz, CDCl₃): δ 1.42 (m, 15 H), 1.63 (m, 7 H), 1.83 (m, 1 H), 1.99 (m, 1 H), 2.60 (m, 4 H), 2.79 (m, 1 H), 3.38 (m, 1 H), 3.87 (m, 6 H), 4.52 (m, 2 H), 6.74 (m, 3 H), 7.22 (m, 5 H).

9-t-Butoxycarbonyl-3,9-diaza-3-[2-(3-(phenylpropyl)-5-(3,4,5-trimethoxyphenyl)pentyl]bicyclo[3.3.1]-nonan-2-one

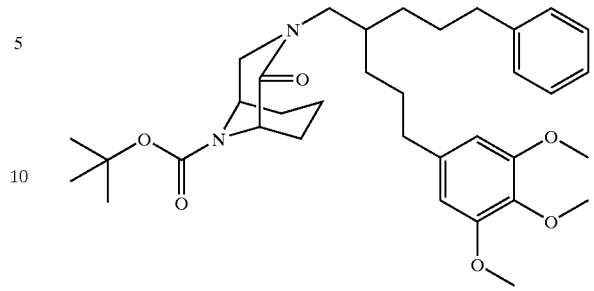

To a solution of 9-t-butoxycarbonyl-3,9-diazabicyclo[3.3.1]nonan-2-one (0.254 g, 1.06 mmol) in tetrahydrofuran (7 mL) was added sodium hydride (60% dispersion in mineral oil, 74.3 mg, 1.86 mmol). After 30 min., 4-bromomethyl-7-phenyl-1-(3,4,5-trimethoxyphenyl)heptane (0.711 g, 1.63 mmol) in tetrahydrofuran (4 mL) and tetrabutylammonium iodide (37.1 mg, 0.100 mmol) were added and the reaction was heated to reflux under nitrogen for 16 h. The mixture was treated with water and extracted with methylene chloride. The combined organic layers were dried over magnesium sulfate, concentrated, and purified by silica gel chromatography, eluting with ethyl acetate/hexanes (30% to 40%), to afford the product (0.516 g, 82%).
¹H NMR (300 MHz, CDCl₃): δ 1.30 (m, 4 H), 1.48 (s, 9 H), 1.75 (m, 11 H), 2.53 (t, 2 H, J=7.5), 2.60 (t, 2 H, J=7.6), 2.99 (d, 1 H, J=12.1), 3.22 (m, 1 H), (m, 1 H), 3.62 (m, 1 H), 3.85 (m, 9 H), 4.52 (m, 2 H), 6.39 (s, 2 H), 7.23 (m, 5 H). MS ESI⁺: m/z 595 (M+H)⁺.

9-t-Butoxycarbonyl-3,9-diaza-3-[5-phenyl-2-(3-phenylpropyl)pentyl]bicyclo[3.3.1]nonan-2-one

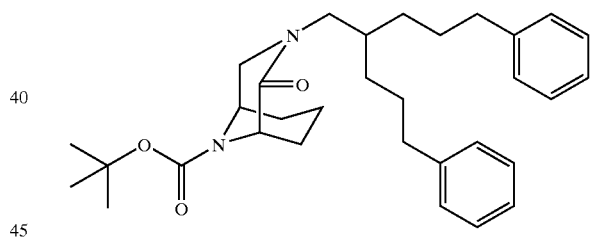

¹H NMR (300 MHz, CDCl₃): δ 1.35 (m, 4H), 1.48 (s, 9 H), 1.75 (m, 11 H), 2.59 (t, 4 H, J=7.5), 2.97 (d, 1 H, J=12.1), 3.21 (dd, 1 H, J=7.3, 13.1), 3.40 (dd, 1 H, J=7.3, 13.3), 3.60 (m, 1 H), 4.52 (m, 2 H), 7.23 (m, 10 H). MS ESI⁺: m/z 505 (M+H)⁺.

9-t-Butoxycarbonyl-3,9-diaza-3-[5-(3,4-dimethoxyphenyl)-2-(3-(3,4-dimethoxyphenyl)propyl)pentyl]bicyclo-[3.3.1]nonan-2-one

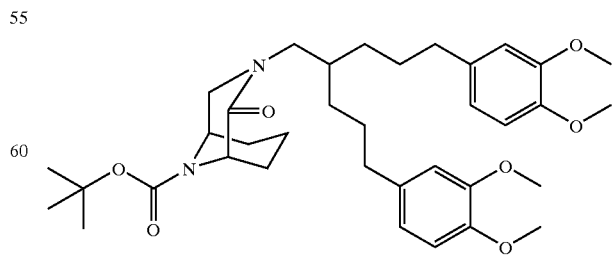

¹H NMR (300 MHz, CDCl₃): δ 1.34 (m, 6 H), 1.47 (s, 9 H), 1.61 (m, 8 H), 1.84 (m, 3 H), 2.54 (t, 4 H, J=7.5), 3.00

(d, 2 H, J=12.1), 3.21 (dd, 1 H, J=7.3, 13.5), 3.42 (dd, 1 H, J=7.5, 13.5), 3.63 (m, 1 H), 3.87 (m, 6 H), 3.88 (m, 6 H), 4.50 (m, 2 H), 6.75 (m, 6 H).
9-t-Butoxycarbonyl-3,9-diaza-3-[4-(3,4-dimethoxyphenyl)-2-((3,4-dimethoxyphenyl)methyl)butyl]bicyclo-[3.3.1]nonan-2-one

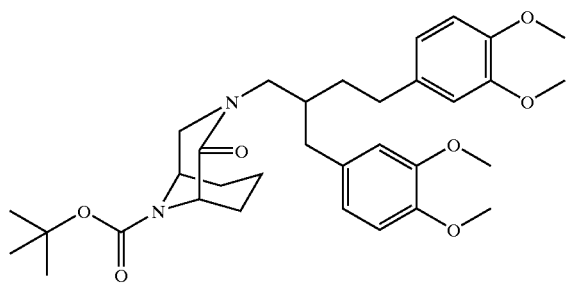

¹H NMR (300 MHz, CDCl₃): δ 1.44 (s, 9 H), 1.66 (m, 8 H), 1.99 (m, 1 H), 2.62 (m, 4 H), 2.90 (m, 1 H), 3.17 (m, 1 H), 3.64 (m, 2 H), 3.86 (m, 12 H), 4.54 (m, 2 H), 6.65 (m, 4 H), 6.79 (m, 2 H). MS ESI⁺: m/z 583 (M+H)⁺.
9-t-Butoxycarbonyl-3,9-diaza-3-[4-(3,4-dimethoxyphenyl)-2-(2-phenylethyl)butyl]bicyclo[3.3.1]nonan-2-one

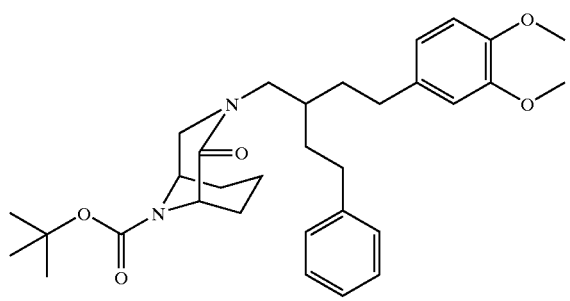

¹H NMR (300 MHz, CDCl₃): δ 1.44 (m, 9 H), 1.78 (m, 11 H), 2.63 (m, 4 H), 2.93 (m, 1 H), 3.49 (m, 3 H), 3.88 (m, 6 H), 4.53 (m, 2 H), 6.75 (m, 3 H), 7.23 (m, 10 H). MS ESI⁺: m/z 537 (M+H)⁺.
Methyl-2-{3,8-diaza-2-oxo-3-[3-(3,4,5-trimethoxyphenyl)propyl]bicyclo[3.2.1]oct-8-yl}-2-oxoacetate

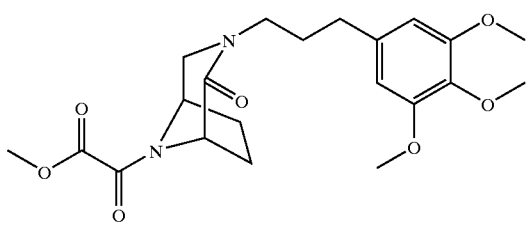

To a suspension of (1S,5R)-8-benzyl-3,8-diaza-3-[3-(3,4,5-trimethoxyphenyl)propyl]bicyclo[3.2.1]octan-2-one (0.122 g, 0.279 mmol) and 10% palladium on carbon (0.100 g) in methanol (7 mL) was added ammonium formate (0.106 g, 1.67 mmol). The resulting mixture was heated at reflux under nitrogen. After 1.5 h the catalyst was removed by filtration through a pad of celite and the solvents were removed under vacuum. The residue was dissolved in dry methylene chloride (3 mL). To this was added methyl oxalyl chloride (50 μL, 0.544 mmol), followed by diisopropylethylamine (0.135 mL, 0.775 mmol). The mixture was stirred at room temperature for 1 h and then concentrated in vacuo. The residue was chromatographed on silica, eluting with ethyl acetate, to give the product as a yellow oil (0.104 g, 97%).
¹H NMR (300 MHz, CDCl₃): δ 1.81 (m, 3 H), 2.23 (m, 3 H), 2.54 (t, 2 H, J=7.8), 3.02 (m, 1 H), 3.34 (m, 2 H), 3.74 (m, 1 H), 3.85 (m, 12 H), 4.82 (m, 1 H), 4.98 (m, 1 H), 6.49 (s, 2 H).
(1S,5R)-8-(3,4,5-Trimethoxyphenyl)oxalyl-3,8-diaza-3-[3-(1,1,2,2-tetramethyl-1-silapropoxy]bicyclo[3.2.1]octan-2-one

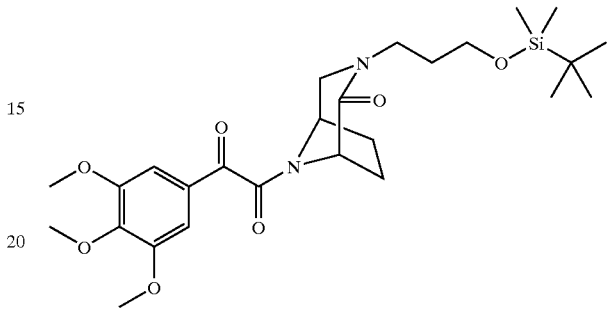

This intermediate was prepared using the same procedure as described for Example 1 below. ¹H NMR (300 MHz, CDCl₃): δ 0.06 (m, 6 H), 0.90 (m, 9 H), 1.77 (m, 3 H), 2.22 (m, 3 H), 3.10 (m, 1 H), 3.29 (m, 1 H), 3.49 (m, 1 H), 3.65 (t, 2 H, J=6.1), 3.82 (m, 1 H), 3.93 (m, 9 H), 4.34 (m, 1 H), 5.09 (m, 1 H), 7.28 (m, 2 H).
Preparation of Fluoresceinated FKBP12 Ligand for Fluorescence Polarization Assay of FKBP12 Binding
N-t-Butyloxycarbonyl-3amino-1-propanol

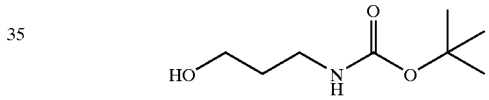

A solution of 3-amino-1-propanol (20.0 g, 266 mmol) in anhydrous dichloromethane (200 mL) was treated with di-t-butyl-dicarbonate (19.4 g, 88.8 mmol) and stirred at ambient temperature overnight. The solvent was evaporated and the residual oil partitioned between diethyl ether and saturated sodium bicarbonate. The organic layer was washed with water, and brine, dried, and evaporated to afford the product as a thick, colorless oil (13.2 g, 85%). ¹H NMR (300 MHz, CDCl₃) δ 4.87 (br s, 1 H), 3.62 (q, 2 H), 3.21 (q, 2 H), 1.61 (m, 2 H), 1.41 (s, 9 H).
N-t-butyloxycarbonyl-3-amino-propionaldehyde

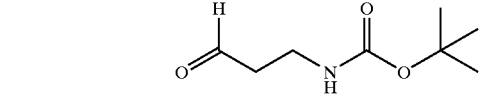

To a stirred solution of the N-t-butyloxycarbonyl-aminopropanol (15.0 g, 65.6 mmol) in dichloromethane (260 mL) at 0° C. was slowly added Dess-Martin periodinane reagent (47.3 g, 111 mmol). The mixture was allowed to gradually warm to ambient temperature and stirred overnight. It was then partitioned between diethyl ether (600 ml) and 1N sodium hydroxide (300 mL) and shaken vigorously. The organic layer was dried and evaporated. The residue was chromatographed on silica, eluting with 25% ethyl acetate/hexane to afford the product as a thin, colorless oil (4.20 g, 28%). ¹H NMR (300 MHz, CDCl₃) δ 9.63 (s, 1 H), 5.17 (br s, 1 H), 3.30 (q, 2 H), 2.60 (t, 2 H), 1.33 (s, 9 H).

1-Phenyl-6-(t-butyloxycarbonyl-amino)-4-hexanol

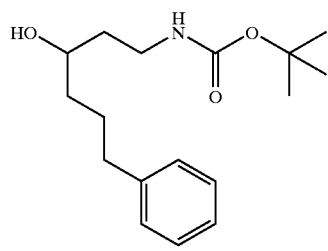

A stirred solution of the N-t-butyloxycarbonyl-aminopropionaldehyde (2.00 g, 11.5 mmol) in tetrahydrofuran under nitrogen at −78° C. was treated with a solution of 3-phenylpropyl Grignard reagent [prepared from magnesium turnings (0.56 g, 23.0 mmol) in tetrahydrofuran (30 mL) treated with 1-bromo-3-phenylpropane (4.60 g, 23.0 mmol) and dibromoethane (100 μL) and stirred at ambient temperature for 1 hour] via syringe over 20 minutes. The mixture was allowed to gradually warm to room temperature and stirred overnight. It was then treated with saturated ammonium hydroxide (5 mL) and evaporated. The residue was taken up in ethyl acetate and washed with water, and brine, dried, and evaporated. The resulting viscous oil was chromatographed on silica, eluting with 20% ethyl acetate/hexane to afford the product as a clear oil (0.075 g, 22%). $^1$H NMR (300 MHz, CDCl$_3$) δ 7.23 (m, 2 H), 7.19 (m, 3 H), 4.82 (br s, 1 H), 3.77 (m, 1 H), 3.19–3.01 (m, 2 H), 2.60 (m, 2 H), 1.88–1.57 (m, 4 H), 1.54–1.44 (m, 2 H), 1.43 (s, 9 H).

1-Phenyl-6-(t-butyloxycarbonyl-amino)-4-hexyl-(S)-N-(t-pentylglyoxyl)pipecolate

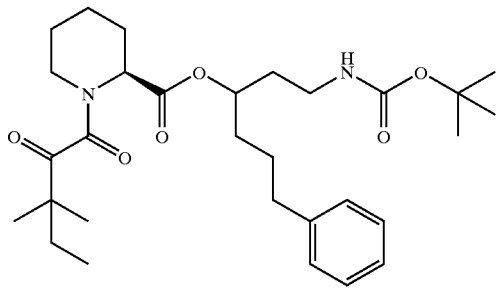

A stirred solution of (S)-N-(t-pentylglyoxyl)-pipecolic acid (0.073 g, 0.25 mmol) and alcohol 1-phenyl-6-(t-butyloxycarbonyl-amino)-4-hexanol (0.069 g, 0.27 mmol) in dichloromethane (1 mL) at 0° C. was treated with 1-[3-(dimethylamino)propyl]-3-ethylcarbodiimide hydrochloride and 4-dimethylaminopyridine and left to stand at ambient temperature overnight. The solution was applied directly to a silica gel column and eluted with 20% ethyl acetate/hexane to afford the ester as a clear oil (0.048 g, 36%). $^1$H NMR (300 MHz, CDCl$_3$) δ 7.23 (m, 2 H), 7.18 (m, 3 H), 5.21 (t, 1 H), 5.06 (br s, 1 H), 4.81 (br s, 1 H), 4.43 (d, 0.5 H), 4.17 (t, 0.5 H), 3.41–3.07 (br m, 3 H), 2.97 (m, 1 H), 2.61 (m, 2 H), 2.29 (t, 1 H), 1.82–1.58 (br m, 10 H), 1.42 (s, 9 H), 1.31 (m, 2 H), 1.18 (m, 6 H), 0.84 (m, 3 H).

1-Phenyl-6-(fluoresceinylaminothiocarbamoyl)-4-hexyl-(S)-N-(t-pentylglyoxyl)pipecolate

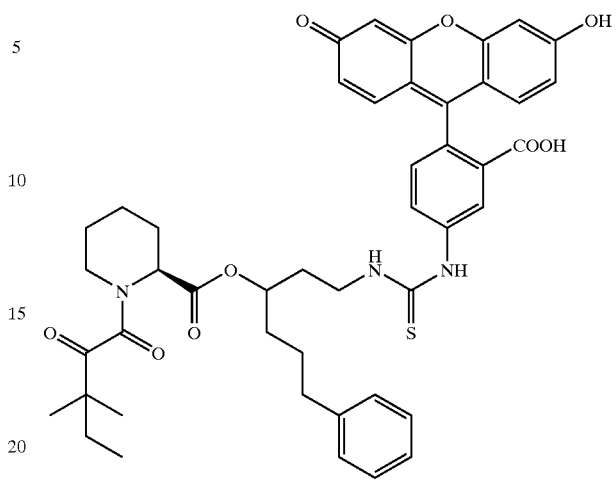

A solution of 1-phenyl-6-(t-butyloxycarbonyl-amino)-4-hexyl-(S)-N-(t-pentylglyoxyl)pipecolate (0.045 g, 0.085 mmol) in neat triflouroacetic acid (2 mL) was stirred at room temperature for 1 hour. Trifluoroacetic acid was removed by rotary evaporation and chased several times with dichloromethane to afford a light film. The residue was taken up in dichloromethane (2 mL), treated with fluorescein isothiocyanate (0.033 g, 0.085 mmol) and triethylamine (0.036 mL, 0.255 mmol), and stirred at room temperature for 3 hours. The resulting solution was diluted with ethyl acetate (10 mL) and washed with 2% phosphoric acid (2 mL), dried, and evaporated. The solid residue was chromatographed on silica, eluting with 1:1:0.01 dichloromethane/ethyl acetate/acetic acid to afford the product as a deep red solid (0.026 g, 37%). $^1$H NMR (300 MHz, deuterated dimethyl sulfoxide) δ 10.74 (br s, 1 H), 9.95 (br s, 1 H), 8.01 (s, 1 H), 8.52 (br s, 1 H), 7.75 (d, 1 H), 7.28–7.16 (m, 7 H), 6.64 (m, 2 H), 6.61–6.58 (m, 5 H), 5.12 (br s, 1 H), 5.03 (br s, 1 H), 3.69–3.18 (br m, 4 H), 3.17–3.01 (br t, 1 H), 2.59 (br s, 2 H), 2.29–2.17 (br t, 2 H), 1.98–1.69 (br m, 2 H), 1.68–1.51 (br s, 6 H), 1.41–1.28 (br s, 2 H), 1.17 (m, 6 H), 0.80 (t, 3 H); HPLC-MS (C-18, methanol/water/trifluoroacetic acid linear gradient elution, 5 mL/min, 220 nm) single peak at 2.16 min; MS (ES$^+$) obsd m/z=820.33.

EXAMPLES

Example 1

(1S,5R)-8-(3,4,5-Trimethoxyphenyl)oxalyl-3,8-diaza-3-(3-phenylpropyl)bicyclo[3.2.1]octan-2-one

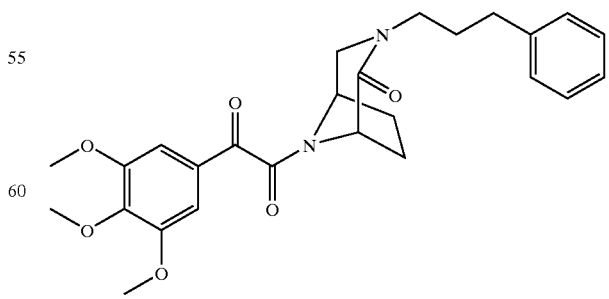

To a suspension of (1S,5R)-8-benzyl-3,8-diaza-3-(3-phenylpropyl)bicyclo[3.2.1]octan-2-one (65.7 mg, 0.196 mmol) and 10% palladium on carbon (67.4 mg) in methanol (5 mL) was added ammonium formate (69.3 mg, 1.10 mmol). The resulting mixture was heated at reflux under nitrogen. After 1.5 h the catalyst was removed by filtration through a pad of celite and the solvents were removed under vacuum. The residue was dissolved in dry methylene chloride (3 mL). To this was added a solution of 3,4,5-trimethoxyphenyl-2-oxoacetyl chloride (1.4 equiv.) in methylene chloride (4 mL), followed by diisopropylethylamine (0.125 mL, 3 equiv.). The mixture was stirred at room temperature for 1.5 h and then concentrated in vacuo. The residue was chromatographed on silica, eluting with 80% ethyl acetate/hexanes, to give the product as a yellow oil (71.6 mg, 78%). $^1$H NMR (300 MHz, CDCl$_3$): δ 1.85 (m, 3 H), 2.25 (m, 3 H), 2.64 (t, 2 H, J=7.7), 3.02 (m, 1 H), 3.31 (m, 1 H), 3.44 (m, 1 H), 3.90 (m, 10 H), 4.34 (m, 1 H), 5.09 (m, 1 H), 7.25 (m, 7 H). MS ESI$^+$: m/z 467 (M+H)$^+$.

Example 2
(1S,5R)-8-(3,4,5-Trimethoxyphenyl)oxalyl-3,8-diaza-3-[2-(3,4-dimethoxyphenyl)ethyl]bicyclo[3.2.1]octan-2-one

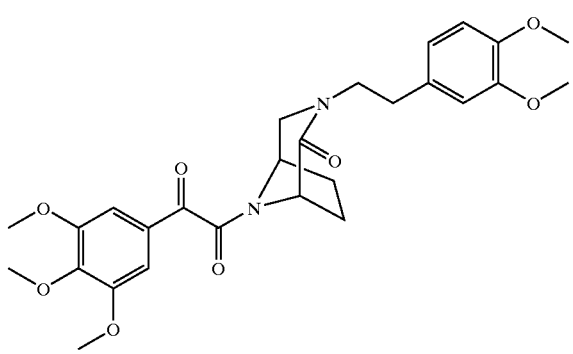

$^1$H NMR (300 MHz, CDCl$_3$): δ 1.63 (m, 2 H), 2.14 (m, 3 H), 2.81 (m, 3 H), 3.29 (m, 1 H), 3.62 (m, 1 H), 3.91 (m, 15 H), 4.26 (m, 1 H), 5.05 (m, 1 H), 6.79 (m, 3 H), 7.27 (s, 2 H). MS ESI$^+$: m/z 513 (M+H)$^+$.

Example 3
(1S,5R)-8-(3,4,5-Trimethoxyphenyl)oxalyl-3,8-diaza-3-[3-(3,4-dimethoxyphenyl)propyl]bicyclo[3.2.1]octan-2-one

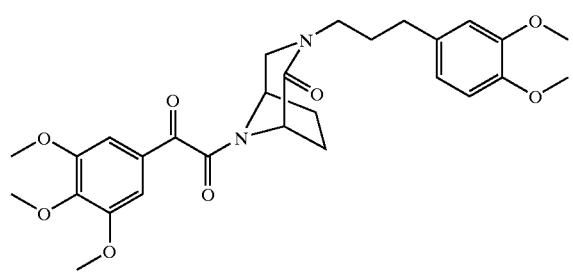

$^1$H NMR (300 MHz, CDCl$_3$): (rotamers) δ 1.82 (m, 3 H), 2.25 (m, 3 H), 2.57 (m, 2 H), 2.97 (d, 0.5 H, J=11.4), 3.06 (d, 0.5 H, J=11.4), 3.36 (m, 2 H), 3.78 (m, 1 H), 3.90 (m, 15 H), 4.33 (m, 1 H), 5.09 (d, 1 H, J=6.0), 6.72 (m, 2 H), 6.79 (d, 1 H, J=8.6), 7.27 (d, 2 H, J=5.7). MS ESI$^+$: m/z 527 (M+H)$^+$.

Example 4
(1S,5R)-8-(3,4,5-Trimethoxyphenyl)oxalyl-3,8-diaza-3-[4-(3,4-dimethoxyphenyl)butyl]bicyclo[3.2.1]octan-2-one

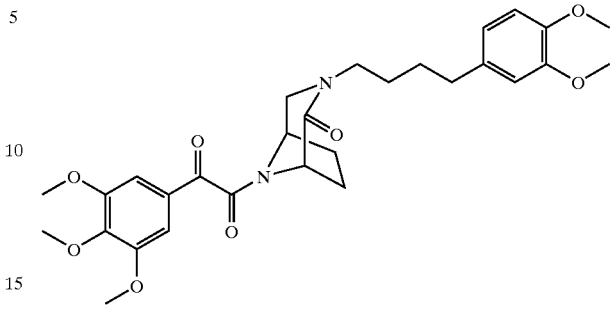

$^1$H NMR (300 MHz, CDCl$_3$): (rotamers) δ 1.58 (m, 4 H), 1.84 (m, 1 H), 2.22 (m, 3 H), 2.59 (t, 2 H, J=6.7), 2.95 (d, 0.5 H, J=11.5), 3.04 (d, 0.5 H, J=11.5), 3.26 (m, 1 H), 3.43 (m, 1 H), 3.74 (m, 1 H), 3.91 (m, 15 H), 4.33 (m, 1 H), 5.10 (m, 1 H), 6.74 (m, 2 H), 7.27 (s, 3 H). MS ESI$^+$: m/z 541 (M+H)$^+$.

Example 5
(1S,5R)-8-(3,4,5-Trimethoxyphenyl)oxalyl-3,8-diaza-3-[3-phenyl-1-(2-phenylethyl)propyl]bicyclo[3.2.1]octan-2-one

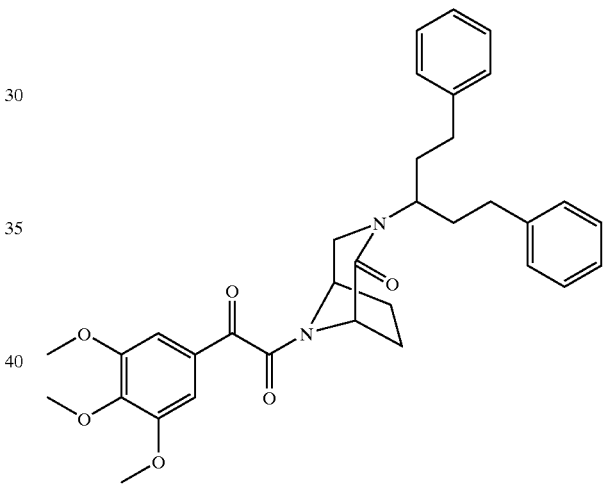

$^1$H NMR (300 MHz, CDCl$_3$): δ 1.82 (m, 5 H), 2.30 (m, 3 H), 2.55 (m, 4 H), 3.00 (m, 1 H), 3.85 (m, 10 H), 4.45 (m, 1 H), 4.67 (m, 1 H), 5.19 (m, 1 H), 7.25 (m, 12 H). MS ESI$^+$: m/z 571 M+H)$^+$.

Example 6
(1S,5R)-8-(3,4,5-Trimethoxyphenyl)oxalyl-3,8-diaza-3-[3-(3,4,5-trimethoxyphenyl)propyl]bicyclo[3.2.1]octan-2-one

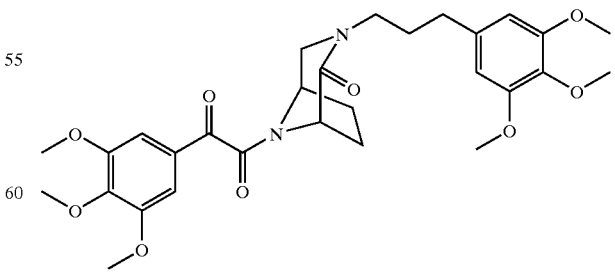

$^1$H NMR (300 MHz, CDCl$_3$): δ 1.59 (m, 1 H), 1.87 (m, 3 H), 2.29 (m, 3 H), 2.59 (m, 2 H), 3.04 (m, 1 H), 3.40 (m, 2 H), 3.85 (m, 18 H), 4.34 (m, 1 H), 5.11 (m, 1 H), 6.43 (s, 2 H), 7.28 (s, 2 H). MS ESI$^+$: m/z 557 (M+H)$^+$.

Example 7
(1S,5R)-8-(3,4,5-Trimethoxyphenyl)oxalyl-3,8-diaza-3-(4-phenylbutyl)bicyclo[3.2.1]octan-2-one

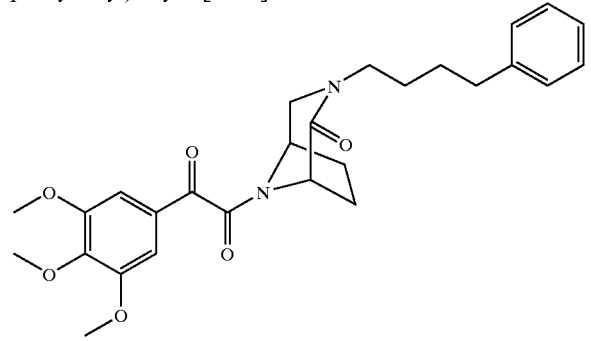

$^1$H NMR (300 MHz, CDCl$_3$): δ 1.60 (m, 4 H), 1.82 (m, 1 H), 2.24 (m, 3 H), 2.65 (m, 2 H), 3.00 (m, 1 H), 3.24 (m, 1 H), 3.46 (m, 1 H), 3.73 (m, 1 H), 3.94 (m, 9 H), 4.34 (m, 1 H), 5.10 (m, 1 H), 7.24 (m, 7 H). MS ESI$^+$: m/z 481 (M+H)$^+$.

Example 8
(1S,5R)-8-(3,4,5-Trimethoxyphenyl)oxalyl-3,8-diaza-3-(3-(3-pyridyloxy)propyl)-bicyclo[3.2.1]octan-2-one

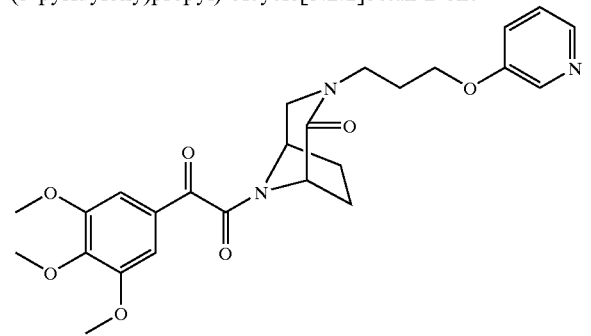

$^1$H NMR (300 MHz, CDCl$_3$): δ 1.90 (m, 1 H), 2.10 (m, 2 H), 2.25 (m, 3 H), 3.13 (m, 1 H), 3.53 (m, 2 H), 3.90 (m, 10 H), 4.20 (m, 2 H), 4.34 (m, 1 H), 5.09 (m, 1 H), 7.26 (m, 4 H), 8.28 (m, 2 H). MS ESI$^+$: m/z 484 (M+H)$^+$.

Example 9
(1S,5R)-8-(3,4,5-Trimethoxyphenyl)oxalyl-3,8-diaza-3-[4-(3,4-dimethoxyphenyl)-1-(3-phenylpropyl)butyl]bicyclo[3.2.1]octan-2-one

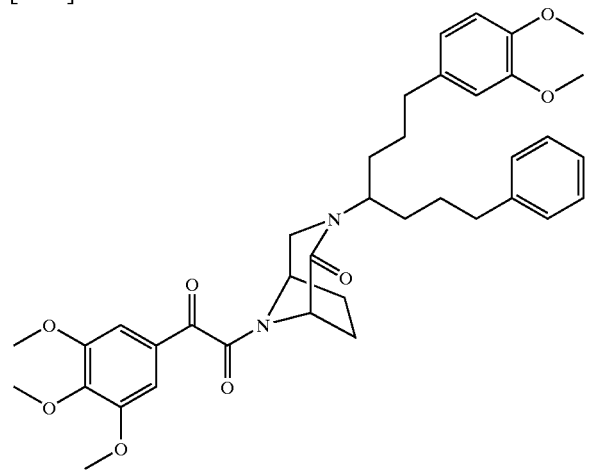

$^1$H NMR (300 MHz, CDCl$_3$): δ1.54 (m, 8 H), 1.75 (m, 1 H), 2.23 (m, 3 H), 2.65 (m, 5 H), 3.47 (m, 1 H), 3.91 (m, 15 H), 4.37 (m, 1 H), 4.64 (m, 1 H), 5.10 (m, 1 H), 6.67 (m, 2 H), 6.78 (m, 1 H), 7.21 (m, 7 H). MS ESI$^+$: m/z 659 (M+H)$^+$.

Example 10
(1S,5R)-8-(3,4,5-Trimethoxyphenyl)oxalyl-3,8-diaza-3-[5-phenyl-2-(3-phenyl-propyl)pentyl]bicyclo[3.2.1]-octan-2-one

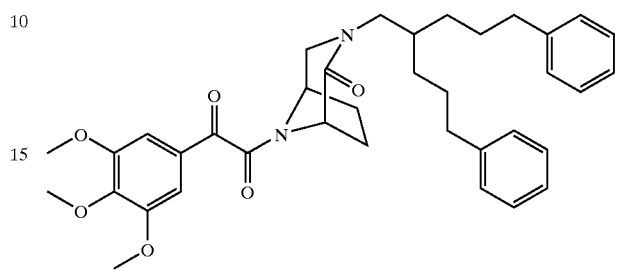

$^1$H NMR (300 MHz, CDCl$_3$): δ 1.30 (m, 4 H), 1.64 (m, 7 H), 2.11 (m, 2 H), 2.58 (m, 4 H), 2.94 (m, 2 H), 3.48 (m, 1 H), 3.62 (m, 1 H), 3.91 (m, 9 H), 4.30 (m, 1 H), 5.05 (m, 1 H), 7.25 (m, 12 H). MS ESI$^+$: m/z 613 (M+H)$^+$.

Example 11
(1S,5R)-8-(3,4,5-Trimethoxyphenyl)oxalyl-3,8-diaza-3-[2-(3-phenylpropyl)-5-(3,4,5-trimethoxyphenyl)pentyl]bicyclo[3.2.1]octan-2-one

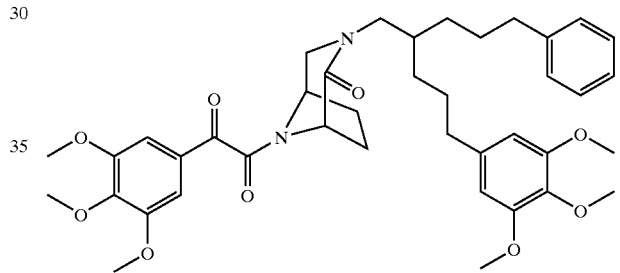

$^1$H NMR (300 MHz, CDCl$_3$): δ 1.33 (m, 4 H), 1.67 (m, 7 H), 2.10 (m, 2 H), 2.53 (t, 2 H, J=7.5), 2.60 (t, 2 H, J=7.4), 3.01 (m, 2 H), 3.47 (m, 1 H), 3.68 (m, 1 H), 3.90 (m, 18 H), 4.30 (m, 1 H), 5.05 (m, 1 H), 6.40 (m, 2 H), 7.18 (m, 3 H), 7.28 (m, 4 H). MS ESI$^+$: m/z 703 (M+H)$^+$.

Example 12
(1S,5R)-8-(3,4,5-Trimethoxyphenyl)oxalyl-3,8-diaza-3-[5-(3,4-dimethoxyphenyl)-2-(3-(3,4-dimethoxyphenyl)propyl)pentyl]bicyclo[3.2.1]octan-2-one

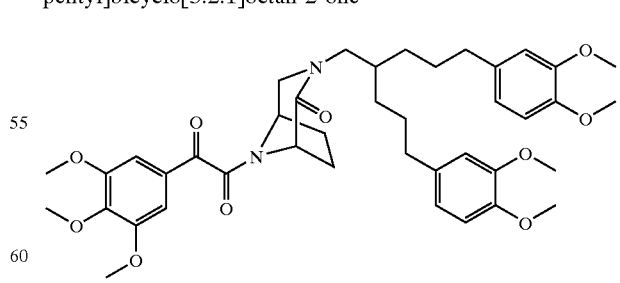

$^1$H NMR (300 MHz, CDCl$_3$): δ 1.33 (m, 4 H), 1.63 (m, 7 H), 2.12 (m, 2 H), 2.54 (m, 4 H), 2.99 (m, 2 H), 3.46 (m, 1 H), 3.69 (m, 1 H), 3.90 (m, 21 H), 4.31 (m, 1 H), 5.06 (m, 1 H), 6.75 (m, 6 H), 7.28 (s, 2 H). MS ESI$^+$: m/z 733 (M+H)$^+$.

Example 13

(1S,5R)-8-(3,4,5-Trimethoxyphenyl)oxalyl-3,8-diaza-3-[4-(3,4-dimethoxyphenyl)-2-((3,4-dimethoxyphenyl)methyl)butyl]bicyclo[3.2.1]octan-2-one

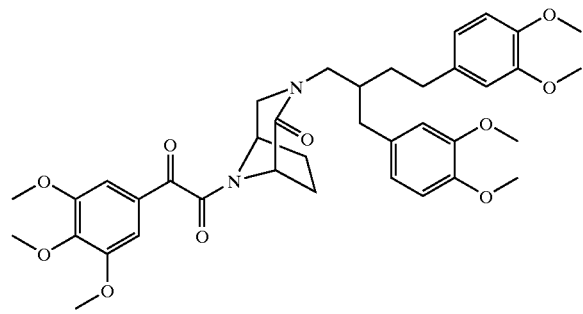

$^1$H NMR (300 MHz, CDCl$_3$): δ 1.69 (m, 3 H), 2.00 (m, 1 H), 2.18 (m, 3 H), 2.60 (m, 4 H), 2.86 (m, 1 H), 3.32 (m, 1 H), 3.58 (m, 2 H), 3.89 (m, 21 H), 4.31 (m, 1 H), 5.07 (m, 1 H), 6.73 (m, 6 H), 7.29 (m, 2 H). MS ESI$^+$: m/z 691 (M+H)$^+$.

Example 14

(1S,5R)-8-(3,4,5-Trimethoxyphenyl)oxalyl-3,8-diaza-3-[4-(3,4-dimethoxyphenyl)-2-(2-phenylethyl)butyl]-bicyclo[3.2.1]octan-2-one

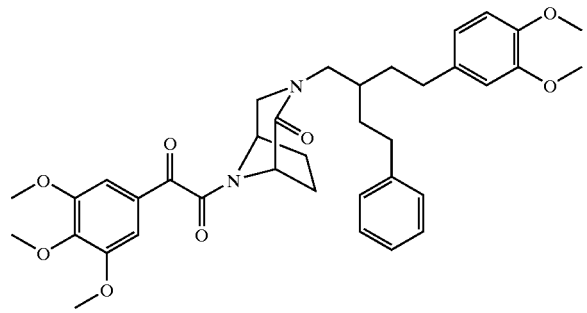

$^1$H NMR (300 MHz, CDCl$_3$): δ 1.58 (m, 6 H), 2.18 (m, 3 H), 2.61 (m, 4 H), 2.86 (m, 1 H), 3.14 (m, 1 H), 3.61 (m, 2 H), 3.87 (m, 15 H), 4.32 (m, 1 H), 5.07 (m, 1 H), 6.71 (m, 3 H), 7.19 (m, 7 H). MS ESI$^+$: m/z 645 (M+H)$^+$.

Example 15

9-(3,4,5-Trimethoxyphenyl)oxalyl-3,9-diaza-3-[3-(3,4,5-trimethoxyphenyl)propyl]bicyclo[3.3.1]nonan-2-one

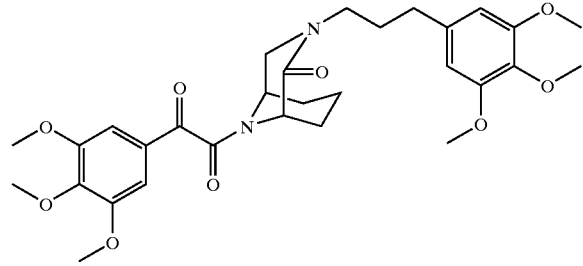

A solution of 9-t-butoxycarbonyl-3,9-diaza-3-[3-(3,4,5trimethoxyphenyl)propyl]-bicyclo[3.3.1]nonan-2-one (73.0 mg, 0.163 mmol) in methylene chloride (5 mL) was treated with 4N HCl in dioxane (0.40 mL, 1.6 mmol). After 2 h the solvents were removed under vacuum. The residue was flushed with dry methylene chloride (3×25 mL), dried in vacuo for 1 h, and dissolved in dry methylene chloride (5 mL). To this was added a solution of 3,4,5-trimethoxyphenyl-2-oxoacetyl chloride (1.4 equiv.) in methylene chloride (5 mL), followed by diisopropylethylamine (0.105 mL, 4 equiv.). The mixture was stirred at room temperature for 1.5 h and then concentrated in vacuo. The residue was chromatographed on silica, eluting with ethyl acetate, to give the product as a yellow oil (64.1 mg, 69%). $^1$H NMR (300 MHz, CDCl$_3$): (rotamers) δ 1.80 (m, 8 H), 2.61 (m, 1.5 H), 3.14 (m, 0.5 H), 3.25 (m, 2 H), 3.67 (m, 2 H), 3.85 (m, 18 H), 4.19 (m, 0.5 H), 4.01 (m, 0.5 H), 5.23 (m, 0.5 H), 5.09 (m, 0.5 H), 6.43 (s, 2 H), 7.20 (s, 1 H), 7.23 (s, 1 H). MS ESI$^+$: m/z 571 (M+H)$^+$.

Example 16

9-(3,4,5-Trimethoxyphenyl)oxalyl-3,9-diaza-3-[3-(3,4-dimethoxyphenyl)propyl]bicyclo[3.3.1]nonan-2-one

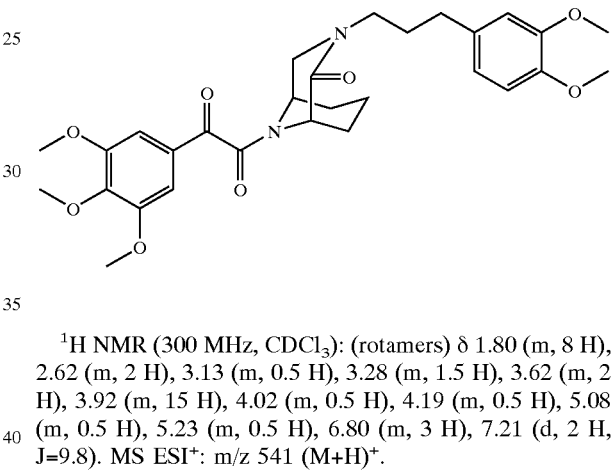

$^1$H NMR (300 MHz, CDCl$_3$): (rotamers) δ 1.80 (m, 8 H), 2.62 (m, 2 H), 3.13 (m, 0.5 H), 3.28 (m, 1.5 H), 3.62 (m, 2 H), 3.92 (m, 15 H), 4.02 (m, 0.5 H), 4.19 (m, 0.5 H), 5.08 (m, 0.5 H), 5.23 (m, 0.5 H), 6.80 (m, 3 H), 7.21 (d, 2 H, J=9.8). MS ESI$^+$: m/z 541 (M+H)$^+$.

Example 17

9-(3,4,5-Trimethoxyphenyl)oxalyl-3,9-diaza-3-[4-(3,4-dimethoxyphenyl)butyl]bicyclo[3.3.1]-nonan-2-one

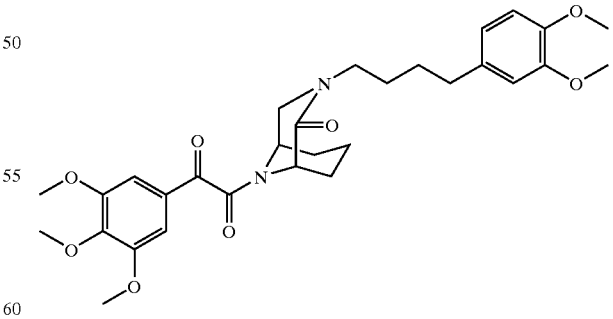

$^1$H NMR (300 MHz, CDCl$_3$): (rotamers) δ 1.65 (m, 5 H), 1.84 (m, 5 H), 2.62 (m, 2 H), 3.11 (d, 0.5 H, J=12.2), 3.27 (m, 1.5 H), 3.72 (m, 2 H), 3.92 (m, 15 H), 4.00 (m, 0.5 H), 4.18 (m, 0.5 H), 5.08 (m, 0.5 H), 5.21 (m, 0.5 H), 6.77 (m, 3 H), 7.21 (d, 2 H, J=9.8). MS ESI$^+$: m/z 555 (M+H)$^+$.

Example 18
9-(3,4,5-Trimethoxyphenyl)oxalyl-3,9-diaza-3-(3-phenylpropyl)bicyclo[3.3.1]nonan-2-one

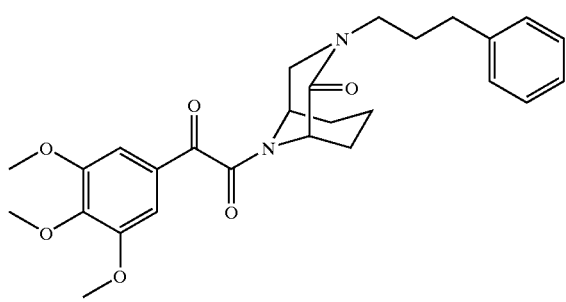

¹H NMR (300 MHz, CDCl₃): (rotamers) δ 1.90 (m, 8 H), 2.66 (m, 2 H), 3.21 (m, 2 H), 3.72 (m, 2 H), 3.91 (m, 9 H), 4.00 (m, 0.5 H), 4.18 (m, 0.5 H), 5.07 (m, 0.5 H), 5.21 (m, 0.5 H), 7.26 (m, 7 H). MS ESI⁺: m/z 481 (M+H)⁺.

Example 19
9-(3,4,5-Trimethoxyphenyl)oxalyl-3,9-diaza-3-(4-phenylbutyl)bicyclo[3.3.1]nonan-2-one

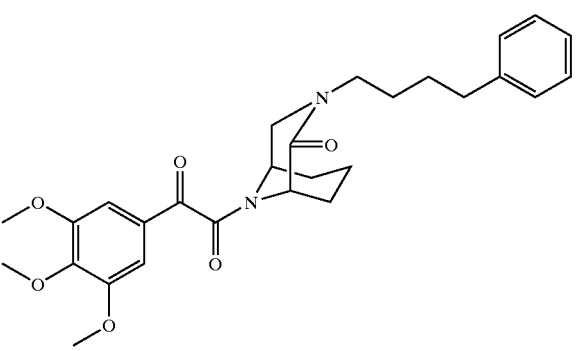

¹H NMR (300 MHz, CDCl₃): (rotamers) δ 1.81 (m, 10 H), 2.67 (m, 2 H), 3.17 (m, 2 H), 3.71 (m, 2 H), 3.90 (m, 9 H), 3.98 (m, 0.5 H), 4.17 (m, 0.5 H), 5.07 (m, 0.5 H), 5.21 (m, 0.5 H), 7.24 (m, 7 H). MS ESI⁺: m/z 495 (M+H)⁺.

Example 20
9-(3,4,5-Trimethoxyphenyl)oxalyl-3,9-diaza-3-(5-phenylpentyl)bicyclo[3.3.1]nonan-2-one

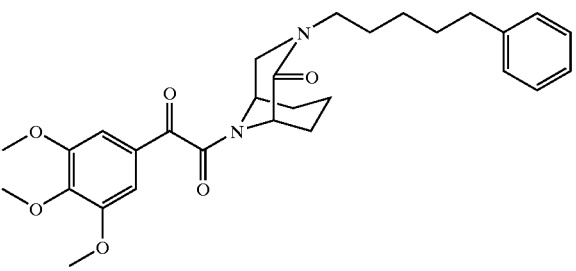

¹H NMR (300 MHz, CDCl₃): (rotamers) δ 1.38 (m, 2 H), 1.80 (m, 10 H), 2.63 (t, 2 H, J=7.6), 3.18 (m, 2 H), 3.70 (m, 2 H), 3.92 (m, 9 H), 3.96 (m, 0.5 H), 4.15 (m, 0.5 H), 5.07 (m, 0.5 H), 5.20 (m, 0.5 H), 7.25 (m, 7 H). MS ESI⁺: m/z 509 (M+H)⁺.

Example 21
9-(3,4,5-Trimethoxyphenyl)oxalyl-3,9-diaza-3-[4-(3,4-dimethoxyphenyl)-1-(3-phenylpropyl)butyl]bicyclo[3.3.1]nonan-2-one

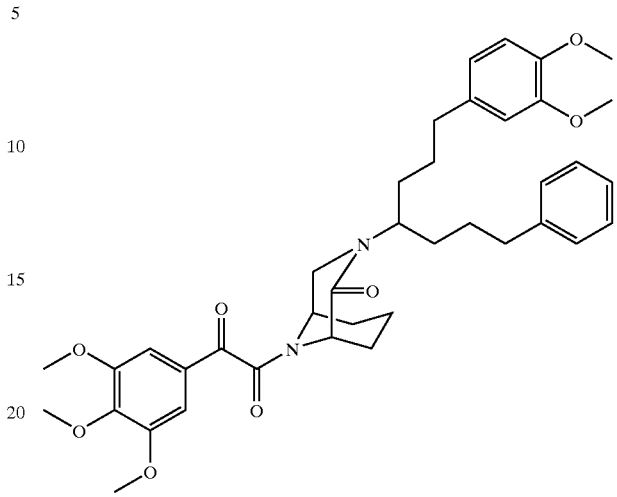

¹H NMR (300 MHz, CDCl₃): δ 1.55 (m, 9 H), 1.80 (m, 4 H), 2.22 (m, 1 H), 2.63 (m, 4 H), 2.89 (m, 1 H), 3.42 (m, 1 H), 3.91 (m, 15 H), 4.10 (m, 1 H), 4.77 (m, 1 H), 5.15 (m, 1 H), 6.73 (m, 3 H), 7.20 (m, 7 H). MS ESI⁺: m/z 673 (M+H)⁺.

Example 22
9-(3,4,5-Trimethoxyphenyl)oxalyl-3,9-diaza-3-[5-phenyl-2-(3-phenylpropyl)pentyl]bicyclo[3.3.1]nonan-2-one

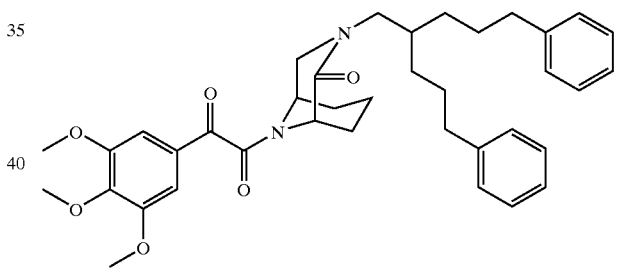

¹H NMR (300 MHz, CDCl₃): (rotamers) δ 1.32 (m, 4 H), 1.78 (m, 11 H), 2.59 (t, 4 H, J=7.1), 3.09 (m, 2 H), 3.61 (m, 2 H), 3.94 (m, 9 H), 4.15 (m, 1 H), 5.01 (m, 0.5 H), 5.20 (m, 0.5 H), 7.25 (m, 12 H). MS ESI⁺: m/z 627 (M+H)⁺.

Example 23
9-(3,4,5-Trimethoxyphenyl)oxalyl-3,9-diaza-3-[2-(3-phenylpropyl)-5-(3,4,5-trimethoxyphenyl)pentyl]bicyclo[3.3.1]-nonan-2-one

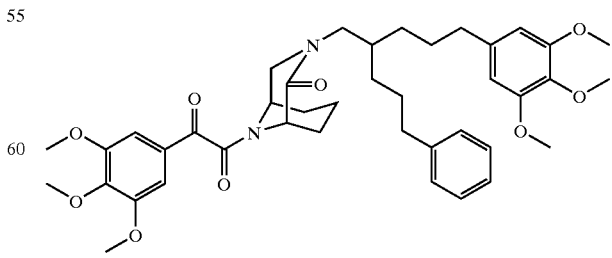

¹H NMR (300 MHz, CDCl₃): (rotamers) δ 1.35 (m, 4 H), 1.76 (m, 11 H), 2.57 (m, 4 H), 3.11 (m, 2 H), 3.58 (m, 2 H),

Example 24
9-(3,4,5-Trimethoxyphenyl)oxalyl-3,9-diaza-3-[5-(3,4-dimethoxyphenyl)-2-(3-(3,4-dimethoxy-phenyl)propyl)pentyl]bicyclo-[3.3.1]nonan-2-one

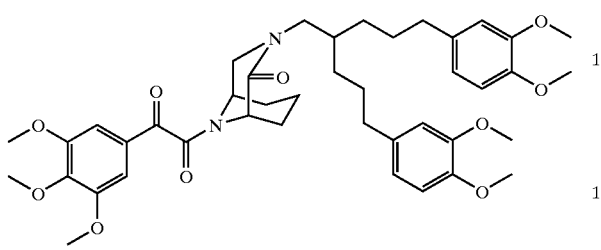

$^1$H NMR (300 MHz, CDCl$_3$): δ 1.34 (m, 4 H), 1.71 (m, 11 H), 2.54 (m, 4 H), 3.08 (m, 2 H), 3.60 (m, 2 H), 3.91 (m, 21 H), 4.15 (m, 1 H), 5.11 (m, 1 H), 6.75 (m, 6 H), 7.24 (m, 2 H). MS ESI$^+$: m/z 747 (M+H)$^+$.

Example 25
9-(3,4,5-Trimethoxyphenyl)oxalyl-3,9-diaza-3-[4-(3,4-dimethoxyphenyl)-2-((3,4-dimethoxy-phenyl)methyl)butyl]bicyclo-[3.3.1]nonan-2-one

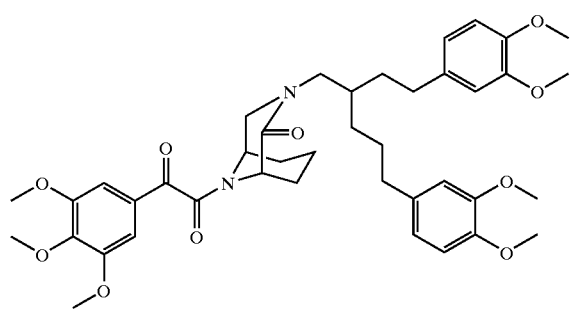

$^1$H NMR (300 MHz, CDCl$_3$): δ 1.74 (m, 7 H), 2.08 (m, 2 H), 2.61 (m, 4 H), 2.95 (m, 1 H), 3.15 (m, 1 H), 3.68 (m, 2 H), 3.90 (m, 21 H), 5.13 (m, 1 H), 6.73 (m, 6 H), 7.22 (m, 3 H). MS ESI$^+$: m/z 705 (M+H)$^+$.

Example 26
9-(3,4,5-Trimethoxyphenyl)oxalyl-3,9-diaza-3-[4-(3,4-dimethoxyphenyl)-2-(2-phenylethyl)butyl]-bicyclo[3.3.1]nonan-2-one

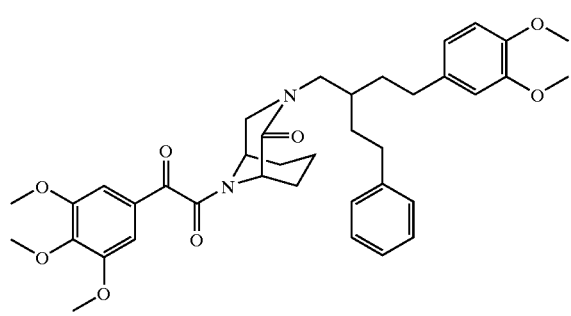

$^1$H NMR (30 MHz, CDCl$_3$): (rotamers) δ 1.77 (m, 10 H), 2.68 (m, 4 H), 3.01 (m, 1 H), 3.31 (m, 1 H), 3.63 (m, 2 H), 3.92 (m, 15 H), 5.01 (m, 0.5 H), 5.24 (m, 0.5 H), 6.73 (m, 3 H), 7.21 (m, 7 H). MS ESI$^+$: m/z 659 (M+H)$^+$.

Example 27
(1S,5R)-8-(3,4,5-Trimethoxyphenyl)difluoroacetyl-3,8-diaza-3-(3-phenylpropyl)bicyclo[3.2.1]octan-2-one

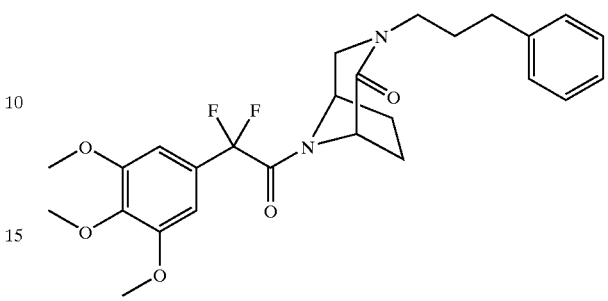

To a suspension of (1S,5R)-8-benzyl-3,8-diaza-3-(3-phenylpropyl)bicyclo[3.2.1]octan-2-one (0.128 g, 0.384 mmol) and 10% palladium on carbon (0.107 g) in methanol (7 mL) was added ammonium formate (0.150 g 2.39 mmol). The resulting mixture was heated at reflux under nitrogen. After 1 h the catalyst was removed by filtration through a pad of celite and the solvents were removed under vacuum. The residue was dissolved in dry methylene chloride (5 mL). To this was added a solution of α,α-difluoro-3,4,5-trimethoxyphenylacetyl chloride (1.4 equiv.) in methylene chloride (3 mL), followed by diisopropylethylamine (0.230 mL, 3 equiv.). The mixture was stirred at room temperature for 1.5 h and then concentrated in vacuo. The residue was chromatographed on silica, eluting with 70% ethyl acetate/hexanes, to give the product as a yellow oil (0.137 g, 73%). $^1$H NMR (300 MHz, CDCl$_3$): δ 1.75 (m, 3 H), 2.13 (m, 3 H), 2.54 (m, 2 H), 2.93 (d, 1 H, J=11.5), 3.25 (m, 2 H), 3.66 (dd, 1 H, J=3.6, 11.4), 3.84 (s, 3 H), 3.87 (s, 6 H), 4.74 (d, 1 H, J=5.5), 5.00 (m, 1 H), 6.77 (s, 2 H), 7.23 (m, 7 H). MS ESI$^+$: m/z 489 (M+H)$^+$.

Example 28
(1S,5R)-8-(3,4,5-Trimethoxyphenyl)difluoroacetyl-3,8-diaza-3-[3-(3,4-dimethoxyphenyl)propyl]bicyclo[3.2.1]octan-2-one

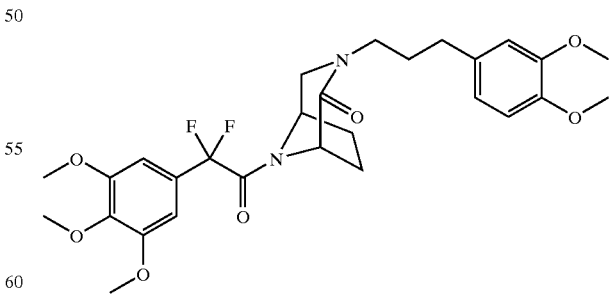

$^1$H NMR (300 MHz, CDCl$_3$): δ 1.70 (m, 3 H), 2.13 (m, 3 H), 2.49 (m, 2 H), 2.94 (d, 1 H, J=11.6), 3.25 (m, 2 H), 3.68 (m, 1 H), 3.87 (m, 15 H), 4.71 (m, 1 H), 5.00 (m, 1 H), 6.82 (m, 5 H). MS ESI$^+$: m/z 549 (M+H)$^+$.

Example 29
(1S,5R)-8-(3,4,5-Trimethoxyphenyl)difluoroacetyl-3,8-diaza-3-[4-(3,4-dimethoxyphenyl)butyl]bicyclo[3.2.1]octan-2-one

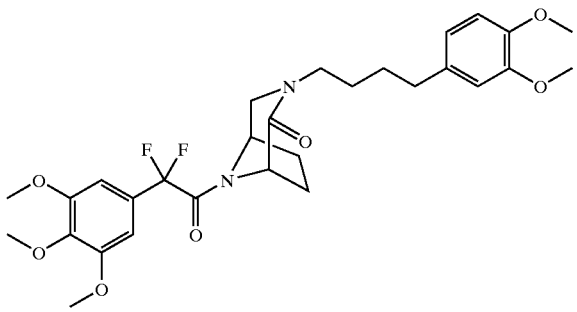

¹H NMR (300 MHz, CDCl₃): δ 1.48 (m, 4 H), 1.74 (m, 1 H), 2.12 (m, 3 H), 2.55 (m, 2 H), 2.90 (d, 1 H, J=11.6), 3.22 (m, 2 H), 3.62 (m, 1 H), 3.87 (m, 15 H), 4.70 (m, 1 H), 5.00 (m, 1 H), 6.74 (m, 5 H). MS ESI⁺: m/z 563 (M+H)⁺.

Example 30
(1S,5R)-8-(3,4,5-Trimethoxyphenyl)difluoroacetyl-3,8-diaza-3-[3-phenyl-1-(2-phenylethyl)propyl]bicyclo[3.2.1]octan-2-one

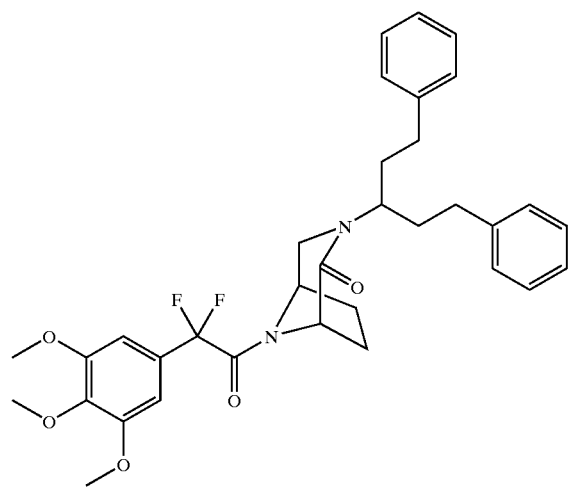

¹H NMR (300 MHz, CDCl₃): δ 1.73 (m, 5 H), 2.20 (m, 5 H), 2.53 (m, 3 H), 2.90 (d, 1 H, J=11.6), 3.58 (dd, 1 H, J=4.0, 11.6), 3.75 (s, 3 H), 3.80 (s, 6 H), 4.94 (d, 1 H, J=5.1), 5.08 (m, 1 H), 6.77 (s, 2 H), 7.18 (m, 10 H). MS ESI⁺: m/z 593 (M+H)⁺.

Example 31
(1S,5R)-8-(3,4,5-Trimethoxyphenyl)difluoroacetyl-3,8-diaza-3-[3-(3,4,5-trimethoxyphenyl)propyl]bicyclo[3.2.1]octan-2-one

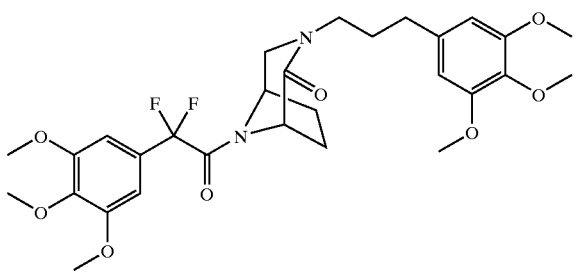

¹H NMR (300 MHz, CDCl₃): δ 1.73 (m, 4 H), 2.10 (m, 3 H), 2.47 (m, 2 H), 2.93 (d, 1 H, J=12.6), 3.26 (m, 2 H), 3.85 (m, 18 H), 4.70 (m, 1 H), 4.99 (m, 1 H), 6.37 (s, 2 H), 6.75 (s, 2 H). MS ESI⁺: m/z 579 (M+H)⁺.

Example 32
(1S,5R)-8-(3,4,5-Trimethoxyphenyl)difluoroacetyl-3,8-diaza-3-(4-phenylbutyl)bicyclo-[3.2.1]octan-2-one

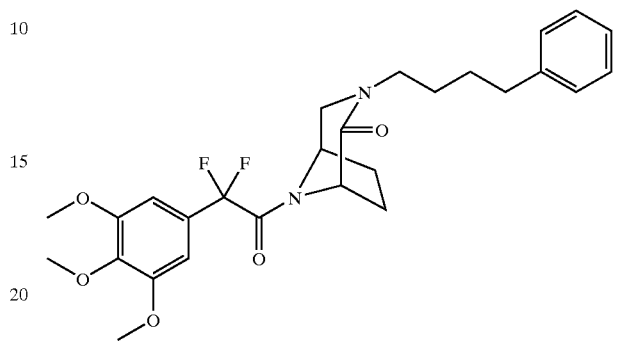

¹H NMR (300 MHz, CDCl₃): δ 1.51 (m, 4 H), 1.74 (m, 1 H), 2.10 (m, 3 H), 2.62 (m, 2 H), 2.90 (d, 1 H, J=11.5), 3.23 (m, 2 H), 3.62 (m, 1 H), 3.90 (m, 9 H), 4.73 (m, 1 H), 5.02 (m, 1 H), 6.78 (s, 2 H), 7.18 (m, 3 H), 7.29 (m, 2 H). MS ESI⁺: m/z 503 (M+H)⁺.

Example 33
(1S,5R)-8-(3,4,5-Trimethoxyphenyl)difluoroacetyl-3,8-diaza-3-[5-phenyl-2-(3-phenyl-propyl)pentyl]bicyclo[3.2.1]-octan-2-one

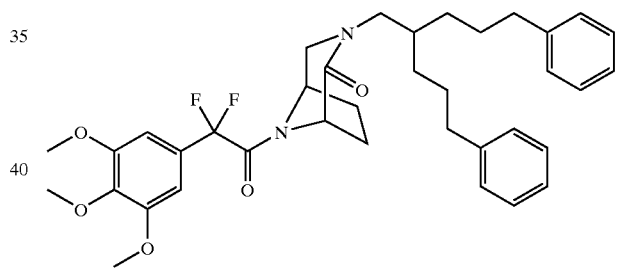

¹H NMR (300 MHz, CDCl₃): 1.25 (m, 4 H), 1.55 (m, 7 H), 1.98 (m, 2 H), 2.57 (t, 4 H, J=6.9), 2.88 (m, 2 H), 3.34 (dd, 1 H, J=8.2, 13.4), 3.52 (dd, 1 H, J=3.7, 11.5), 3.88 (m, 9 H), 4.62 (m, 1 H), 4.98 (m, 1 H), 6.77 (s, 2 H), 7.23 (m, 10 H). MS ESI⁺: m/z 635 (M+H)⁺.

Example 34
(1S,5R)-8-(3,4,5-Trimethoxyphenyl)difluoroacetyl-3,8-diaza-3-[2-(3-phenylpropyl)-5-(3,4,5-trimethoxyphenyl)pentyl]bicyclo[3.2.1]octan-2-one

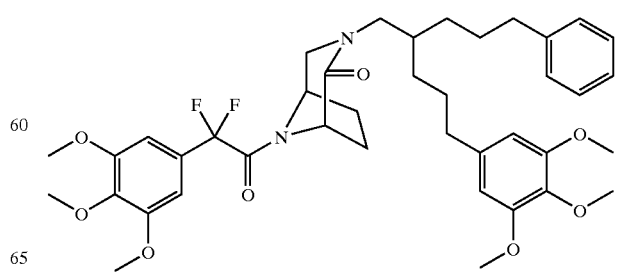

¹H NMR (300 MHz, CDCl₃): δ 1.25 (m, 4 H), 1.59 (m, 7 H), 1.99 (m, 2 H), 2.54 (m, 4 H), 2.95 (m, 2 H), 3.31 (m, 1 H), 3.57 (m, 1 H), 3.87 (m, 18 H), 4.63 (m, 1 H), 4.98 (m, 1 H), 6.38 (d, 2 H, J=4.6), 6.77 (s, 2 H), 7.23 (m, 5 H). MS ESI⁺: m/z 725 (M+H)⁺.

Example 35

9-(3,4,5-Trimethoxyphenyl)difluoroacetyl-3,9-diaza-3-[3-(3,4-dimethoxyphenyl)propyl]bicyclo[3.3.1]nonan-2-one

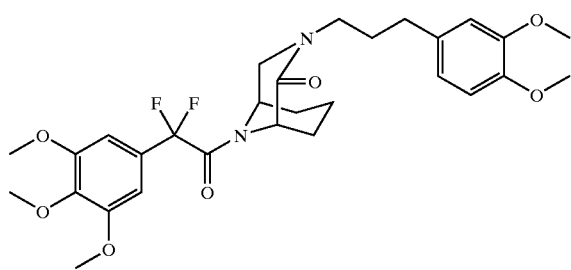

¹H NMR(300 MHz, CDCl₃): (rotamers) δ 1.64 (m, 3 H), 1.89 (m, 4 H), 2.59 (m, 2 H), 3.09 (m, 1 H), 3.29 (m, 2 H), 3.55 (m, 1 H), 3.69 (m, 1 H), 3.89 (m, 15 H), 4.38 (m, 0.5 H), 4.67 (m, 0.5 H), 5.04 (m, 0.5 H), 5.18 (m, 0.5 H), 6.77 (m, 5 H). MS ESI⁺: m/z 563 (M+H)⁺.

Example 36

9-(3,4,5-Trimethoxyphenyl)difluoroacetyl-3,9-diaza-3-[4-(3,4-dimethoxyphenyl)butyl]bicyclo[3.3.1]-nonan-2-one

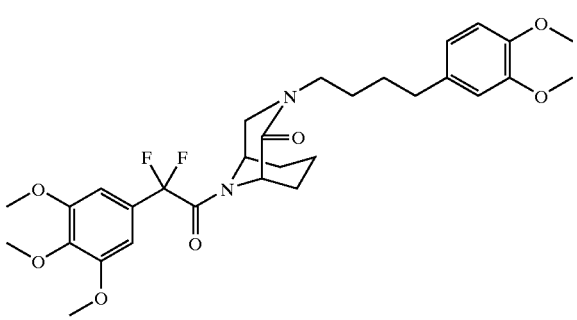

¹H NMR (300 MHz, CDCl₃): (rotamers) δ 1.77 (m, 10 H), 2.60 (m, 2 H), 2.99 (m, 1 H), 3.49 (m, 1 H), 3.59 (m, 2 H), 3.89 (m, 15 H), 4.38 (m, 0.5 H), 4.66 (m, 0.5 H), 5.04 (m, 0.5 H), 5.18 (m, 0.5 H), 6.82 (m, 5 H). MS ESI⁺: m/z 577 (M+H)⁺.

Example 37

9-(3,4,5-Trimethoxyphenyl)difluoroacetyl-3,9-diaza-3-[5phenyl-2-(3-phenylpropyl)pentyl]bicyclo[3.3.1]nonan-2-one

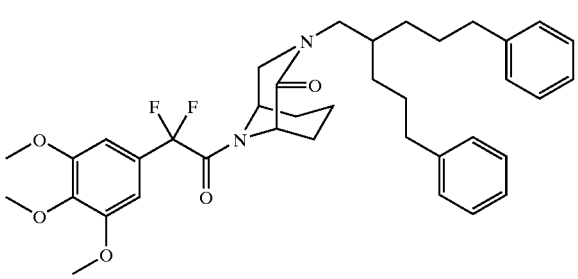

¹H NMR (300 MHz, CDCl₃): (rotamers) δ 1.30 (m, 4 H), 1.70 (m, 11 H), 2.57 (m, 4 H), 3.03 (m, 2 H), 3.36 (m, 1 H), 3.54 (m, 1 H), 3.89 (m, 9 H), 4.32 (m, 0.5 H), 4.65 (m, 0.5 H), 4.96 (m, 0.5 H), 5.15 (m, 0.5 H), 6.76 (m, 2 H), 7.23 (m, 10 H). MS ESI⁺: m/z 649 (M+H)⁺.

Example 38

9-(3,4,5-Trimethoxyphenyl)difluoroacetyl-3,9-diaza-3-[2-(3-phenylpropyl)-5-(3,4,5-trimethoxyphenyl)pentyl]bicyclo[3.3.1]-nonan-2-one

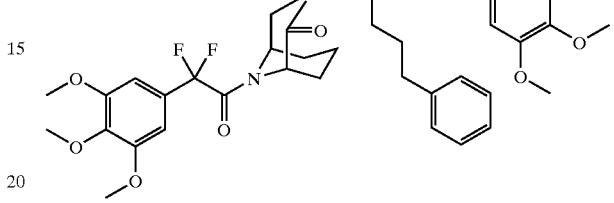

BMS-340598

¹H NMR (300 MHz, CDCl₃): (rotamers) δ 1.30 (m, 4 H), 1.70 (m, 11 H), 2.55 (m, 4 H), 3.01 (m, 2 H), 3.38 (m, 1 H), 3.59 (m, 1 H), 3.85 (m, 18 H), 4.33 (m, 0.5 H), 4.65 (m, 0.5 H), 4.98 (m, 0.5 H), 5.15 (m, 0.5 H), 6.38 (d, 2 H, J=4.1), 6.76 (s, 2 H), 7.22 (m, 5 H). MS ESI⁺: m/z 739 (M+H)⁺.

Example 39

1-{3,8-Diaza-2-oxo-3-[3-(3,4,5-trimethoxyphenyl)propyl]bicyclo[3.2.1]oct-8-yl}-3,3-dimethylpentane-1,2-dione

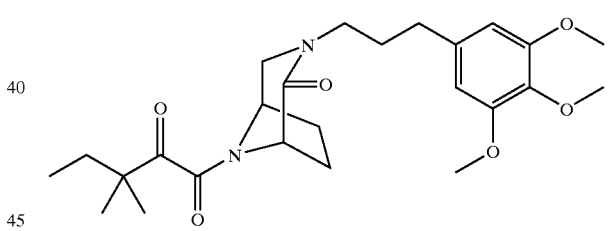

To a solution of the methyl-2-{3,8-diaza-2-oxo-3-[3-(3,4,5-trimethoxyphenyl)propyl]bicyclo[3.2.1]oct-8-yl}-2-oxoacetate (0.104 g, 0.248 mmol) in tetrahydrofuran (3 mL) at −78° C. under nitrogen was added 1,1-dimethylpropylmagnesium chloride (1.0M in ether, 0.300 mL, 0.300 mmol). After 30 min, a second aliquot of 1,1-dimethylpropylmagnesium chloride (1.0M in ether, 0.200 mL, 0.200 mmol) was added. After 15 min., the reaction was quenched with saturated aqueous ammonium chloride and extracted with ethyl acetate. The combined organics were dried over magnesium sulfate and the solvent was removed under reduced pressure. Purification by silica gel chromatography, eluting with ethyl acetate, gave the desired compound (69.7 mg, 61%). ¹H NMR (300 MHz, CDCl₃): δ 0.85 (t, 3 H, J=7.5), 1.17 (s, 3 H), 1.18 (s, 3 H), 1.74 (m, 5 H), 2.19 (m, 3 H), 2.54 (t, 2 H, J=7.7), 2.96 (t, 1 H, J=10.8), 3.36 (m, 2 H), 3.74 (m, 1 H), 3.81 (s, 3 H), 3.84 (s, 6 H), 4.19 (m, 1 H), 4.94 (d, 1 H, J=6.3), 6.39 (s, 2 H). MS ESI⁺: m/z 461 (M+H)⁺.

Example 40
Methyl-2-{3,9-diaza-2-oxo-3-[3-(3,4,5-trimethoxyphenyl)propyl]bicyclo[3.3.1]non-9-yl}-2-oxoacetate

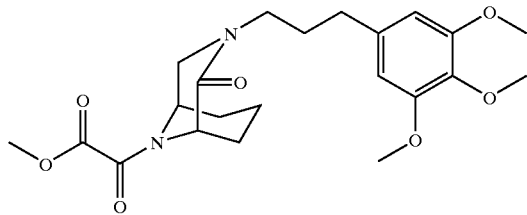

A solution of 9-t-butoxycarbonyl-3,9-diaza-3-[3-(3,4,5-trimethoxyphenyl)propyl]-bicyclo[3.3.1]nonan-2-one (0.189 g, 0.422 mmol) in methylene chloride (5 mL) was treated with 4N HCl in dioxane (1.60 mL, 6.40 mmol). After 2 h the solvents were removed under vacuum. The residue was flushed with dry methylene chloride (3×25 mL), dried in vacuo for 1 h, and dissolved in dry methylene chloride (5 mL). To this was added methyl oxalyl chloride (75 μL, 0.815 mmol), followed by diisopropylethylamine (0.320 mL, 1.79 mmol). The mixture was stirred at room temperature for 1 h and then concentrated in vacuo. The residue was chromatographed on silica, eluting with 75% ethyl acetate/hexanes, to give the product as a yellow oil (0.179 g, 98%). $^1$H NMR (300 MHz, CDCl$_3$): δ 1.84 (m, 7 H), 2.10 (m, 1 H), 2.61 (m, 2 H), 3.20 (m, 1 H), 3.31 (m, 1 H), 3.63 (m, 1 H), 3.76 (m, 1 H), 3.88 (m, 12 H), 4.35 (m, 1 H), 5.05 (m, 1 H), 6.44 (s, 2 H). MS ESI$^+$: m/z 435 (M+H)$^+$.

Example 41
1-{3,9-Diaza-2-oxo-3-[3-(3,4,5-trimethoxyphenyl)propyl]bicyclo[3.3.1]non-9-yl}-3,3-dimethylpentane-1,2-dione

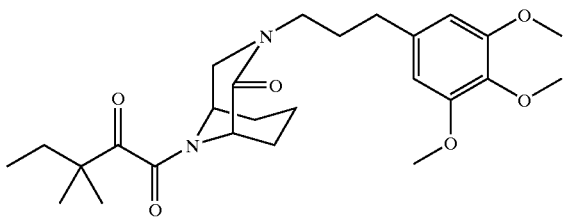

$^1$H NMR (300 MHz, CDCl$_3$): δ 0.88 (m, 3 H), 1.20 (m, 6 H), 1.77 (m, 10 H), 2.05 (m, 1 H), 2.58 (t, 2 H, J=7.5), 3.16 (t, 1 H, J=12.8), 3.45 (m, 2 H), 3.74 (m, H), 3.86 (m, 9 H), 4.99 (m, 1 H), 6.41 (m, 2 H). MS ESI$^+$: m/z 475 (M+H)$^+$.

Example 42
(1S,5R)-8-(3,4,5-trimethoxyphenyl)oxalyl-3,8-diaza-3-(3-hydroxypropyl)bicyclo[3.2.1]octan-2-one

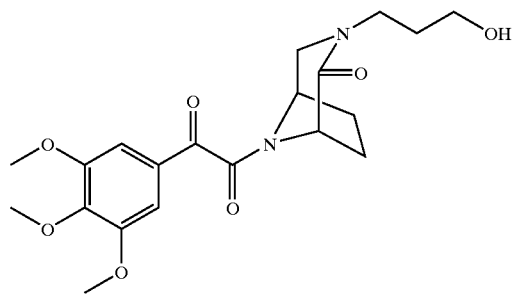

Tetrabutylammonium fluoride (1.0 M in tetrahydrofuran, 3.40 mL, 3.40 mmol) was added to a solution of (1S,5R)-8-(3,4,5-trimethoxyphenyl)oxalyl-3,8-diaza-3-[3-(1,1,2,2-tetramethyl-1-silapropoxy]bicyclo[3.2.1]octan-2-one (1.30 g, 2.49 mmol) in tetrahydrofuran (20 mL) and the resulting solution was stirred for 30 min. The mixture was treated with water and extracted with methylene chloride. The combined organic layers were washed with brine, dried over magnesium sulfate, and concentrated. Purification by silica gel chromatography, eluting with 7.5% methanol/methylene chloride gave the product (0.918 g, 91%). $^1$H NMR (300 MHz, CDCl$_3$): δ 1.75 (m, 2 H), 1.87 (m, 1 H), 2.25 (m, 3 H), 2.80 (s, 1 H), 3.05 (m, 1 H), 3.55 (m, 3 H), 3.75 (m, 2 H), 3.91 (m, 9 H), 4.37 (m, 1 H), 5.11 (m, 1 H), 7.29 (m, 2 H).

Example 43
FKBP12 Rotamase Inhibition Assay

The rotamase activity of FKBP-12 was measured by an adaptation of the assay described by Kofron et al. (*Biochemistry*, 30, pp. 6127–6134 (1991)). The assay was carried out at 4° C. with 1 mg chymotrypsin/mL of assay with succinyl-Ala-Leu-Pro-Phe-p-nitroanilide as the substrate. Chymotrypsin rapidly hydrolyzes the peptide bond on the C-terminal side of the Phe of the trans form of the peptide and releases the chromogenic p-nitroaniline. The rate of the reaction is controlled by the rate of conversion of the cis form of the peptide to the trans-form, the reaction catalyzed by FKBP12. The apparent K$_i$ values for inhibition of the rotamase activity were determined by measuring decreases in the first order rate constant of the reaction catalyzed by FKBP12 as a function of the concentrations of the compounds described herein. K$_i$ is the concentration of the compound that causes 50 percent inhibition of rotamase activity which is indicative of neurite outgrowth activity.

Example 44
Fluorescence Polarization (FP) Assay of FKBP12 Binding

A fluorescent FKBP12 ligand at 100 nM (K$_i$ measured by the prolyl isomerase assay is 32 nM) is mixed with an excess of FKBP12 (200 nM) to ensure a high proportion of bound ligand. The buffer (25 mM HEPES, 100 mM sodium chloride, pH 7.5) with pre-mixed enzyme and fluorescent ligand is distributed into wells (190 μL/well). Inhibitors are added as 10 μL of a 10% dimethylsulfoxide solution in the same buffer. FP is measured with an excitation wavelength of 485 nm and emission wavelength of 520 nm. A comparison of several FKBP12 inhibitors showed that the IC$_{50}$ values obtained by the FP assay are approximately 10-fold higher than those measured by the rotamase assay described in Example 43.

Example 45
Assay of Neurite Outgrowth in PC12 Cell Cultures

PC-12A rat pheochromocytoma cells are maintained in Dulbecco's modified Eagle's medium (DMEM) supplemented with 10% fetal calf serum and 5% calf serum at 37° C. and 5% CO$_2$. Cells to be assayed are plated at 10$^4$ per well of a 24 well plate and allowed to attach for 4–18 h. The medium is then replaced with DMEM plus 0.1% BSA, submaximal concentrations of nerve growth factor (NGF) (as determined by neurite outgrowth assay), and varying concentrations of the FKBP12 binding compound (0.1 nM–10 μM) in a final concentration of 0.25% DMSO. Control cultures are treated with NGF in the absence of the FKBP12 binding compound. After 72 h, cultures are fixed with 4% formalin in PBS, stained with Commassie Blue, and approximately 200 cells are counted in random fields of each well. Cells with neurites longer than one cell diameter are counted as a percentage of total number of cells.

The FKBP12 binding compounds of formula I utilized in this invention cause a significant increase in neurite outgrowth over control cultures.

Additionally, compounds of this invention may also show benefit as reversers of multidrug resistance (MDR) in cancer chemotherapy and as agents for the treatment of HIV infection. Nonimmunosuppressive compounds possessing the structural elements of the FKBP12 binding portion of FK506 have shown utility in reversing P-glycoprotein mediated MDR (U. A. Germann, et al., *Anti-Cancer Drugs,* 8, pp. 125–140 (1997)). In addition, there has been no direct correlation shown between rotamase inhibitory activity and MDR reversing activity (J. R. Hauske, et al., *Bioorg. Med. Chem. Lett.,* 4, pp. 2097–2102 (1994)). In the area of HIV infection, it is known that immunophilins, including the FK506 binding proteins (FKBPs), are involved in facilitating binding of the HIV envelope protein gp120 to host CD4 receptors (M. M. Endrich, et al., *Eur. J. Biochem.,* 252, pp. 441–446 (1998)), and that FK506 inhibits the growth of HIV-infected cells (A. Karpas, et al., *Proc. Natl. Acad. Sci USA,* 89, pp. 8351–8355 (1992)).

TABLE 1

FKBP12 r tamase inhibition data with selected examples.

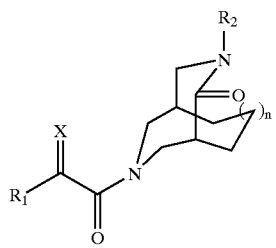

| Ex. # | $R_2$ | $R_1$ | X | n | % FP inhibition at 1 $\mu$M | rotamase $K_i$, nM (from FP) |
|---|---|---|---|---|---|---|
| 39 | 3-(3,4,5-trimethoxyphenyl)propyl | t-butyl | O | 0 | 4 | |
| 41 | 3-(3,4,5-trimethoxyphenyl)propyl | t-butyl | O | 1 | 4 | |
| 1 | 3-phenylpropyl | 3,4,5,-trimethoxyphenyl | O | 0 | 34 | 699 |
| 27 | 3-phenylpropyl | 3,4,5,-trimethoxyphenyl | $F_2$ | 0 | 22 | |
| 18 | 3-phenylpropyl | 3,4,5,-trimethoxyphenyl | O | 1 | | 60 |
| 6 | 3-(3,4,5-trimethoxyphenyl)propyl | 3,4,5,-trimethoxyphenyl | O | 0 | 47 | 242 |
| 31 | 3-(3,4,5-trimethoxyphenyl)propyl | 3,4,5,-trimethoxyphenyl | $F_2$ | 0 | 19 | 598 |
| 15 | 3-(3,4,5-trimethoxyphenyl)propyl | 3,4,5,-trimethoxyphenyl | O | 1 | 44 | 100 |
| 3 | 3-(3,4-dimethoxyphenyl)propyl | 3,4,5,-trimethoxyphenyl | O | 0 | 26 | 380 |
| 28 | 3-(3,4-dimethoxyphenyl)propyl | 3,4,5,-trimethoxyphenyl | $F_2$ | 0 | 13 | |
| 16 | 3-(3,4-dimethoxyphenyl)propyl | 3,4,5,-trimethoxyphenyl | O | 1 | 76 | 150 |
| 35 | 3-(3,4-dimethoxyphenyl)propyl | 3,4,5,-trimethoxyphenyl | $F_2$ | 1 | 47 | 360 |
| 4 | 3-(3,4-dimethoxyphenyl)butyl | 3,4,5,-trimethoxyphenyl | O | 0 | 15 | |
| 29 | 3-(3,4-dimethoxyphenyl)butyl | 3,4,5,-trimethoxyphenyl | $F_2$ | 0 | 8 | |
| 17 | 3-(3,4-dimethoxyphenyl)butyl | 3,4,5,-trimethoxyphenyl | O | 1 | 79 | 140 |
| 36 | 3-(3,4-dimethoxyphenyl)butyl | 3,4,5,-trimethoxyphenyl | $F_2$ | 1 | 61 | 160 |
| 7 | 4-phenylbutyl | 3,4,5,-trimethoxyphenyl | O | 0 | 6 | |
| 32 | 4-phenylbutyl | 3,4,5,-trimethoxyphenyl | $F_2$ | 0 | 4 | |
| 19 | 4-phenylbutyl | 3,4,5,-trimethoxyphenyl | O | 1 | | 85 |
| 2 | 2-(3,4-dimethoxyphenyl)ethyl | 3,4,5,-trimethoxyphenyl | O | 0 | 3 | |
| 20 | 5-phenylpentyl | 3,4,5,-trimethoxyphenyl | O | 1 | | 152 |
| 8 | 3-(3-pyridyloxy)propyl | 3,4,5,-trimethoxyphenyl | O | 1 | 98 | |
| 42 | 3-hydroxypropyl | 3,4,5,-trimethoxyphenyl | O | 1 | 19 | |
| 40 | 3-(3,4,5-trimethoxyphenyl)propyl | methoxy | O | 1 | 6 | |

TABLE 2

FKBP12 rotamase inhibition data with selected examples.

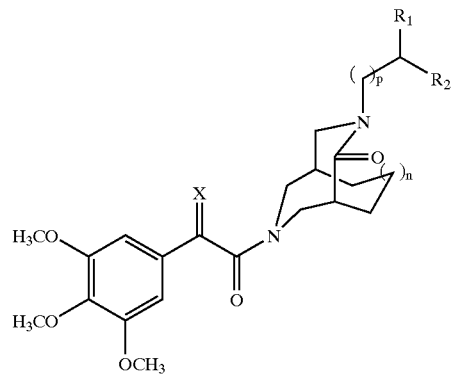

| Ex # | $R_1$ | $R_2$ | X | n | p | % Rotamase inhibition at 1 μM | % FP inhibition at 1 μM | rotamase $K_i$, nM (from FP) |
|---|---|---|---|---|---|---|---|---|
| 11 | 3-(3,4,5-trimethoxyphenyl)propyl | 3-phenylpropyl | O | 0 | 1 | | 17 | |
| 34 | 3-(3,4,5-trimethoxyphenyl)propyl | 3-phenylpropyl | $F_2$ | 0 | 1 | | 11 | |
| 10 | 3-phenylpropyl | 3-phenylpropyl | O | 0 | 1 | | 14 | |
| 37 | 3-phenylpropyl | 3-phenylpropyl | $F_2$ | 0 | 1 | | 4 | |
| 22 | 3-phenylpropyl | 3-phenylpropyl | O | 1 | 1 | | 17 | |
| 33 | 3-phenylpropyl | 3-phenylpropyl | $F_2$ | 1 | 1 | | 7 | |
| 23 | 3-(3,4,5-trimethoxyphenyl)propyl | 3-phenylpropyl | O | 1 | 1 | | 81 | 44 |
| 38 | 3-(3,4,5-trimethoxyphenyl)propyl | 3-phenylpropyl | $F_2$ | 1 | 1 | | 50 | |
| 12 | 3-(3,4-dimethoxyphenyl)propyl | 3-(3,4-dimethoxyphenyl)propyl | O | 0 | 1 | | | 47 |
| 13 | 2-(3,4-dimethoxyphenyl)ethyl | 3,4-dimethoxybenzyl | O | 0 | 1 | | | 122 |
| 14 | 2-(3,4-dimethoxyphenyl)ethyl | 2-phenylethyl | O | 0 | 1 | | | 169 |
| 24 | 2-(3,4-dimethoxyphenyl)propyl | 3-(3,4-dimethoxyphenyl)propyl | O | 1 | 1 | | | 21 |
| 25 | 2-(3,4-dimethoxyphenyl)ethyl | 3,4-dimethoxybenzyl | O | 1 | 1 | | | 18 |
| 26 | 2-(3,4-dimethoxyphenyl)ethyl | 2-phenylethyl | O | 1 | 1 | | | 51 |
| 5 | 2-phenylethyl | 2-phenylethyl | O | 0 | 0 | 49 | | |
| 9 | 3-(3,4-dimethoxyphenyl)propyl | 3-phenylpropyl | O | 0 | 0 | | 1 | |
| 21 | 3-(3,4-dimethoxyphenyl)propyl | 3-phenylpropyl | O | 1 | 0 | | 1 | |
| 30 | 2-phenylethyl | 2-phenylethyl | $F_2$ | 0 | 0 | | 4 | |

If pharmaceutically acceptable salts of the compounds of formula I are used, those salts are preferably derived from inorganic or organic acids and bases. Included among such acid salts are the following: acetate, aspartate, bisulfate, butyrate, citrate, fumarate, hydrochloride, hydrobromide, hydroiodide, lactate, maleate, oxalate, persulfate, propionate, succinate, tartrate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir.

It should also be understood that a specific dosage and treatment regimen for any particular patient will depend upon a variety of factors, including the activity of the specific compound employed, the age, body weight, general health, sex, diet, time of administration, rate of excretion, and the judgment of the treating physician and the severity of the particular disease being treated. The amount of compound of formula I will also depend upon the particular FKBP12 binding compound in the composition.

The amount of compound of formula I utilized in these methods is between about 0.01 and 100 mg/kg body weight/day.

What is claimed is:

1. A compound having the formula (I)

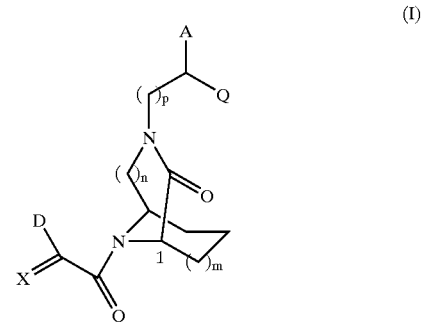

or pharmaceutically acceptable salts thereof, wherein:

X is $F_2$;

n is 1;

m is 1;

p is 0 or 1;

wherein the stereochemistry at carbon position 1 is R or S;

D is $(C_1-C_6)$-straight or branched alkyl, $(C_2-C_6)$-straight or branched alkenyl, $(C_5-C_7)$-cycloalkyl or $(C_5-C_7)$-cycloalkenyl substituted with $(C_1-C_4)$-straight or branched alkyl or $(C_2-C_4)$-straight or branched alkenyl, O—$(C_1-C_4)$-straight or branched alkyl, O—$(C_2-C_4)$-straight or branched alkenyl, 2-indolyl, 3-indolyl, $((C_1-C_4)$-alkyl or $(C_2-C_4)$-alkenyl)-Ar or Ar;

Ar is a carbocyclic aromatic group selected from the group consisiting of phenyl, 1-naphthyl, 2-naphthyl, indenyl, azulenyl, fluorenyl, and anthracenyl; or a heterocyclic aromatic group selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl;

Ar may contain one to three substituents which are independently selected from the group consisting of hydrogen, halogen, hydroxyl, hydroxymethyl, nitro, trifluoromethyl, trifluoromethoxy, $(C_1-C_6)$-straight or branched alkyl, $(C_2-C_6)$-straight or branched alkenyl, O—$((C_1-C_4)$-straight or branched alkyl), O-benzyl, O-phenyl, 1,2-methylenedioxy, amino, carboxyl, N-$((C_1-C_5)$-straight or branched alkyl or $(C_2-C_5)$-straight or branched alkenyl)carboxamides, N,N-di-$((C_1-C_5)$-straight or branched alkyl or $(C_2-C_5)$-straight or branched alkenyl)carboxamides, N-morpholinecarboxamide, N-benzylcarboxamide, N-thiomorpholinocarboxamide, N-picolinoylcarboxamide, O—W, $CH_2$—$(CH_2)_q$—W, O—$(CH_2)_q$—W, $(CH_2)_q$—O—W, and CH=CH—W;

W is 4-methoxyphenyl, 2-pyridyl, 3-pyridyl, 4-pyridyl, pyrazyl, quinolyl, 3,5-dimethylisoxazoyl, isoxazolyl, 2-methylthiazoyl, thiazoyl, 2-thienyl, 3-thienyl, or pyrimidyl; q is 0–2;

Q and A are independently hydrogen, Ar, $(C_1-C_{10})$-straight or branched alkyl, $(C_2-C_{10})$-straight or branched alkenyl or alkynyl, $(C_5-C_7)$-cycloalkyl substituted $(C_1-C_6)$-straight or branched alkyl, $(C_2-C_6)$-straight or branched alkenyl or alkynyl, $(C_5-C_7)$-cycloalkenyl substituted $(C_1-C_6)$-straight or branched alkyl, $(C_2-C_6)$-straight or branched alkenyl or alkynyl, or Ar-substituted $(C_1-C_6)$-straight or branched alkyl, $(C_2-C_6)$-straight or branched alkenyl or alkynyl wherein, in each case, any one of the $CH_2$ groups of said alkyl, alkenyl or alkynyl chains may be optionally replaced by a heteroatom selected from the group consisting of O, S, SO, $SO_2$, N, and NR, wherein R is selected from the group consisting of hydrogen, $(C_1-C_4)$-straight or branched alkyl, $(C_2-C_4)$-straight or branched alkenyl or alkynyl, and $(C_1-C_4)$-bridging alkyl wherein a bridge is formed between the nitrogen and a carbon atom of said heteroatom-containing chain to form a ring, and wherein said ring is optionally fused to an Ar group; or

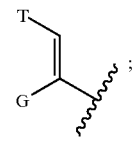

G is hydrogen, $(C_1-C_6)$-straight or branched alkyl or $(C_2-C_6)$-straight or branched alkenyl or alkynyl; and T is Ar or substituted 5–7 membered cycloalkyl with substituents at positions 3 and 4 which are independently selected from the group consisting of oxo, hydrogen, hydroxyl, O—$(C_1-C_4)$-alkyl, or O—$(C_2-C_4)$-alkenyl.

2. A compound of claim 1 wherein:

the stereochemistry at carbon 1 is S;

m is 1;

n is 1;

p is 1;

X is $F_2$;

D is 3,4,5-trimethoxyphenyl or t-pentyl;

Q and A are independently hydrogen; 2, 3, or 4-pyridyl; or phenyl-substituted $(C_1-C_6)$-straight or branched chain alkyl, wherein phenyl is optionally substituted with one to three substituents independently selected from $(C_1-C_6)$ alkyl, O—$(C_1-C_6)$ alkyl, carboxyl and trifluoromethyl, wherein said alkyl is straight or branched.

3. A compound of claim 1 wherein:

the stereochemistry at carbon 1 is S;

m is 1;

n is 1;

p is 1;

A is 3-phenylpropyl, 2-phenylethyl, 2-(3,4-dimethoxyphenyl)ethyl, 3-(3,4,5-trimethoxyphenyl)propyl or 3-(3,4-dimethoxyphenyl)propyl; and Q is 3-phenylpropyl, 2-phenylethyl, 3-(3,4,5-trimethoxyphenyl)propyl, 2-(3,4-dimethoxyphenyl)ethyl or 3-(3,4-dimethoxyphenyl)propyl.

4. A compound of claim 1 wherein:

the stereochemistry at carbon 1 is S;

m is 1;

n is 1;

p is 0;

A is hydrogen; and

Q is 2-(3,4,5-trimethoxyphenyl)ethyl, 2-(3,4-dimethoxyphenyl)ethyl, 3-(3,4-dimethoxyphenyl)propyl, 2-phenylethyl, 3-phenylpropyl, 4-phenylbutyl or 2-(3-pyridyloxy)ethyl.

5. A pharmaceutical composition which comprises as an active ingredient an amount of a compound as claimed in any one of claims 1 to 4, or a pharmaceutically acceptable salt thereof, effective for stimulating neurite growth in nerve cells, and one or more pharmaceutically acceptable carriers, excipients or diluents thereof.

6. A method for stimulating neurite growth in nerve cells comprising the step of contacting said nerve cells with a composition comprising a neurotrophic amount of a compound with affinity for an FK506 binding protein as claimed in any one of claims 1–4.

7. A method for stimulating neurite growth in nerve cells comprising the step of contacting said nerve cells with a composition comprising a neurotrophic amount of a compound with affinity for FKBP12 as claimed in any one of claims 1–4.

* * * * *